United States Patent [19]

Hubele

[11] Patent Number: 4,931,560
[45] Date of Patent: Jun. 5, 1990

[54] PESTICIDES

[75] Inventor: Adolf Hubele, Magden, Switzerland

[73] Assignee: Ciba-Geigy Corporation, Ardsley, N.Y.

[21] Appl. No.: 247,203

[22] Filed: Sep. 21, 1988

[30] Foreign Application Priority Data

Sep. 28, 1987 [CH] Switzerland ............ 3750/87-2
Apr. 11, 1988 [CH] Switzerland ............ 1333/88-5

[51] Int. Cl.$^5$ .......................... C07D 239/02
[52] U.S. Cl. .................. 544/315; 544/316; 544/318; 544/334; 514/275; 424/405
[58] Field of Search ........... 424/405; 544/242, 243, 544/315, 316, 318, 334

[56] References Cited

U.S. PATENT DOCUMENTS 4,764,611  8/1988  Baasner et al. ............ 544/242

FOREIGN PATENT DOCUMENTS 0224339  6/1987  European Pat. Off. .
151404    6/1980  Fed. Rep. of Germany .
3319843   6/1984  Fed. Rep. of Germany ...... 544/242

Primary Examiner—Ellis P. Robinson
Assistant Examiner—P. L. Prater
Attorney, Agent, or Firm—Edward McC. Roberts

[57] ABSTRACT

Compounds of the formula

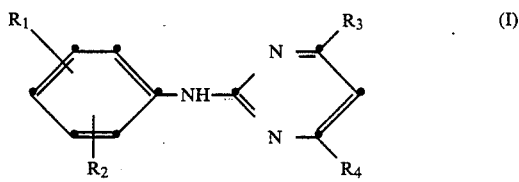

in which:
R$_1$ and R$_2$ independently of one another are hydrogen, halogen, C$_1$–C$_3$alkyl, C$_1$–C$_2$haloalkyl, C$_1$–C$_3$alkoxy or
C$_1$–C$_3$haloalkoxy; R$_3$ is hydrogen; C$_1$–C$_4$alkyl; or C$_1$–C$_4$alkyl substituted by halogen, hydroxy or by cyano; cyclopropyl; or cyclopropyl mono- to tri-substituted by methyl and/or by halogen; and R$_4$ is C$_3$–C$_6$cycloalkyl or
C$_3$–C$_6$cycloalkyl mono- to tri-substituted by methyl and/or by halogen, have valuable microbicidal and insecticidal properties. The novel active ingredients can be used in plant protection for preventing an attack on cultivated plants by phytopathogenic microorganisms or by harmful insects, and for controlling these pests.

1 Claim, No Drawings

PESTICIDES

The present invention relates to novel 2-anilinopyrimidine derivatives of formula I below. It relates also to the preparation of those substances and to agrochemical compositions that contain as active ingredient at least one of those compounds. The invention relates also to the preparation of the mentioned compositions and to the use of the active ingredients or of the compositions for controlling pests, especially harmful insects and plant-destructive microorganisms, preferably fungi.

The compounds according to the invention correspond to the general formula I

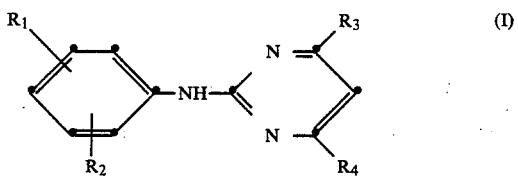

in which:
$R_1$ and $R_2$ independently of one another are hydrogen, halogen, $C_1$–$C_3$alkyl, $C_1$–$C_2$haloalkyl, $C_1$–$C_3$alkoxy or $C_1$–$C_3$haloalkoxy; $R_3$ is hydrogen; $C_1$–$C_4$alkyl; or $C_1$–$C_4$alkyl substituted by halogen, hydroxy and/or cyano; cyclopropyl; or cyclopropyl mono- to tri-substituted by methyl and/or by halogen; and $R_4$ is $C_3$–$C_6$cycloalkyl or $C_3$–$C_6$cycloalkyl mono- to tri-substituted by methyl and/or by halogen; including their acid addition salts and metal salt complexes.

Depending on the number of carbon atoms indicated, alkyl by itself or as a component of another substituent, such as haloalkyl, alkoxy or haloalkoxy, is to be understood as meaning, for example, methyl, ethyl, propyl, butyl and their isomers, such as, for example, isopropyl, isobutyl, tert.-butyl or sec.-butyl. Halogen, also called Hal, is fluorine, chlorine, bromine or iodine. Haloalkyl and haloalkoxy are mono- to perhalogenated radicals, such as, for example. $CHCl_2$, $CH_2F$, $CCl_3$, $CH_2Cl$, $CHF_2$, $CF_3$, $CH_2CH_2Br$, $C_2Cl_5$, $CH_2Br$, $CHBrCl$ etc., preferably $CF_3$. Depending on the number of carbon atoms indicated, cycloalkyl is, for example, cyclopropyl, cyclobutyl, cyclopentyl or cyclohexyl.

N-pyrimidinylaniline compounds are already known. For example, in published European patent application No. 0 224 339 and in GDR patent specification No. 151 404, compounds that have an N-2-pyrimidinyl structure are described as being effective against plant-destructive fungi. However, the known compounds have hitherto been unable fully to meet the demands made of them in practice. The characteristic difference between the compounds of formula I according to the invention and the known compounds is that at least one cycloalkyl radical and other substituents have been introduced into the anilinopyrimidine structure, as a result of which an unexpectedly high fungicidal activity and insecticidal action is obtained with the novel compounds.

The compounds of formula I are oils, resins or solids that are stable at room temperature and that are distinguished by valuable microbicidal properties. They can be used preventively and curatively in the agricultural sector or related fields for controlling plant-destructive micro-organisms. The compounds of formula I according to the invention are distinguished at low application concentrations not only by excellent insecticidal and fungicidal action but also by the fact that they are especially well tolerated by plants.

The invention relates both to the free compounds of formula I and to their addition salts with inorganic and organic acids and to their complexes with metal salts.

Salts according to the invention are especially addition salts with acceptable inorganic or organic acids, for example hydrohalic acids, for example hydrochloric, hydrobromic or hydriodic acid, sulfuric acid, phosphoric acid, phosphorous acid, nitric acid, or organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

Metal salt complexes of formula I consist of the organic molecule on which they are based and an inorganic or organic metal salt, for example the halides, nitrates, sulfates, phosphates, acetates, trifluoroacetates, trichloroacetates, propionates, tartrates, sulfonates, salicylates, benzoates etc. of the elements of the second main group, such as calcium and magnesium, and of the third and fourth main groups, such as aluminum, tin or lead, and of the first to eighth subgroups, such as chromium, manganese, iron, cobalt, nickel, copper, zinc etc. The subgroup elements of the fourth period are preferred. The metals can be in any of their various valencies. The metal complexes can be mono- or polynuclear, that is to say they can contain one or more organic molecular moieties as ligands.

An important group of phytofungicides and insecticides is formed by those of formula I in which $R_1$ and $R_2$ are hydrogen.

A special group is formed by the following compounds of formula I in which:
$R_1$ and $R_2$ independently of one another are hydrogen, halogen, $C_1$–$C_3$alkyl, $C_1$–$C_2$haloalkyl, $C_1$–$C_3$alkoxy or $C_1$–$C_3$haloalkoxy; $R_3$ is hydrogen, $C_1$–$C_4$alkyl or $C_1$–$C_4$alkyl substituted by halogen or by cyano; and $R_4$ is $C_3$–$C_6$cycloalkyl or $C_3$–$C_6$cycloalkyl substituted by methyl or by halogen.

The following groups of active ingredients are preferred because of their pronounced microbicidal, especially phytofungicidal, activity:

GROUP 1a

Compounds of formula I in which:
$R_1$ and $R_2$ independently of one another are hydrogen, fluorine, chlorine, bromine, methyl, ethyl, halomethyl, methoxy, ethoxy or halomethoxy; $R_3$ is hydrogen, methyl, methyl substituted by fluorine, chlorine, bromine or by cyano; ethyl, ethyl substituted by fluorine, chlorine, bromine or by cyano; n-propyl or sec.-butyl; and $R_4$ is $C_3$–$C_6$cycloalkyl or $C_3$–$C_6$cycloalkyl substituted by methyl, fluorine, chlorine or by bromine.

Of the above-mentioned compounds, an especially preferred group is formed by those in which $R_1=R_2=$hydrogen (=Group 1aa).

GROUP 1b

Compounds of formula I in which:

$R_1$ and $R_2$ independently of one another are hydrogen, chlorine, bromine, methyl, ethyl, trifluoromethyl, methoxy, ethoxy or difluoromethoxy; $R_3$ is hydrogen, methyl, methyl substituted by fluorine, chlorine or by cyano, ethyl or n-propyl; and $R_4$ is $C_3$–$C_5$cycloalkyl or $C_3$–$C_5$cycloalkyl substituted by methyl or by chlorine.

Of the above-mentioned compounds, an especially preferred group is formed by those in which $R_1=R_2=$hydrogen (=Group 1$bb$).

GROUP 1$c$

Compounds of formula I in which:

$R_1$ and $R_2$ independently of one another are hydrogen, chlorine, methyl, methoxy, ethoxy or trifluoromethyl; $R_3$ is hydrogen, methyl, ethyl or trifluoromethyl; and $R_4$ is cyclopropyl or cyclopropyl substituted by methyl or by chlorine.

Of the above-mentioned compounds, an especially preferred group is formed by those in which $R_1=R_2=$hydrogen (=Group 1$cc$).

GROUP 1$d$

Compounds of formula I in which:

$R_1$ is hydrogen; $R_2$ and $R_3$ independently of one another are hydrogen or methyl; and $R_4$ is cyclopropyl or cyclopropyl substituted by methyl.

GROUP 2$a$

Compounds of formula I in which:

$R_1$ and $R_2$ independently of one another are hydrogen, halogen, $C_1$–$C_2$alkyl, halomethyl, $C_1$–$C_2$alkoxy or $C_1$–$C_2$haloalkoxy; $R_3$ is hydrogen; $C_1$–$C_4$alkyl; $C_1$–$C_2$alkyl substituted by halogen or by hydroxy; cyclopropyl; or cyclopropyl mono- to tri-substituted by methyl and/or by halogen; and $R_4$ is $C_3$–$C_6$cycloalkyl or $C_3$–$C_4$cycloalkyl mono- to tri-substituted by methyl and/or by halogen.

Of the above-mentioned compounds, an especially preferred group is formed by those in which $R_1=R_2=$hydrogen (=Group 2$aa$).

GROUP 2$b$

Compounds of formula I in which:

$R_1$ and $R_2$ independently of one another are hydrogen, fluorine, chlorine, bromine, methyl, trifluoromethyl, methoxy or difluoromethoxy; $R_3$ is hydrogen; $C_1$–$C_3$alkyl; $C_1$–$C_2$alkyl substituted by halogen or by hydroxy; cyclopropyl; or cyclopropyl mono- to tri-substituted by methyl and/or by halogen; and $R_4$ is $C_3$–$C_6$cycloalkyl or $C_3$–$C_4$cycloalkyl mono- to tri-substituted by methyl and/or by halogen.

Of the above-mentioned compounds, an especially preferred group is formed by those in which $R_1=R_2=$hydrogen (=Group 2$bb$).

GROUP 2$c$

Compounds of formula I in which:

$R_1$ and $R_2$ independently of one another are hydrogen, fluorine, chlorine, methyl, trifluoromethyl, methoxy or difluoromethoxy; $R_3$ is hydrogen; $C_1$–$C_3$alkyl; $C_1$–$C_2$alkyl substituted by halogen or by hydroxy; cyclopropyl; or cyclopropyl mono- to tri-substituted by methyl and/or by halogen; and $R_4$ is $C_3$–$C_6$cycloalkyl or $C_3$–$C_4$cycloalkyl mono-to tri-substituted by methyl and/or by halogen.

Of the above-mentioned compounds, an especially preferred group is formed by those in which $R_1=R_2=$hydrogen (=Group 2$cc$).

GROUP 2$d$

Compounds of formula I in which:

$R_1$ and $R_2$ are hydrogen; $R_3$ is $C_1$–$C_3$alkyl; methyl substituted by fluorine, chlorine, bromine or by hydroxy; cyclopropyl; or cyclopropyl substituted by methyl, fluorine, chlorine or by bromine; and $R_4$ is $C_3$–$C_4$cycloalkyl or $C_3$–$C_4$cycloalkyl mono- to tri-substituted by methyl and/or by fluorine, chlorine or by bromine.

Of the individual substances that are especially preferred there may be mentioned, for example:

2-phenylamino-4-methyl-6-cyclopropylpyrimidine (comp. no. 1.1);
2-phenylamino-4-ethyl-6-cyclopropylpyrimidine (comp. no. 1.6);
2-phenylamino-4-methyl-6-(2-methylcyclopropyl)-pyrimidine (comp. no. 1.14);
2-phenylamino-4,6-bis(cyclopropyl)pyrimidine (comp. no. 1.236);
2-phenylamino-4-hydroxymethyl-6-cyclopropylpyrimidine (comp. no. 1.48);
2-phenylamino-4-fluoromethyl-6-cyclopropylpyrimidine (comp. no. 1.59);
2-phenylamino-4-hydroxymethyl-6-(2-methylcyclopropyl)-pyrimidine (comp. no. 1.13);
2-phenylamino-4-methyl-6-(2-fluorocyclopropyl)-pyrimidine (comp. no. 1.66);
2-phenylamino-4-methyl-6-(2-chlorocyclopropyl)-pyrimidine (comp. no. 1.69);
2-phenylamino-4-methyl-6-(2-difluorocyclopropyl)-pyrimidine (comp. no. 1.84);
2-phenylamino-4-fluoromethyl-6-(2-fluorocyclopropyl)-pyrimidine (comp. no. 1.87);
2-phenylamino-4-fluoromethyl-6-(2-chlorocyclopropyl)-pyrimidine (comp. no. 1.94);
2-phenylamino-4-fluoromethyl-6-(2-methylcyclopropyl)-pyrimidine (comp. no. 1.108);
2-phenylamino-4-ethyl-6-(2-methylcyclopropyl)-pyrimidine (comp. no. 1.131);
2-(p-fluorophenylamino)-4-methyl-6-cyclopropyl-pyrimidine (comp. no. 1.33).

The compounds of formula I are prepared as follows:
1. a phenylguanidine salt of formula II$a$

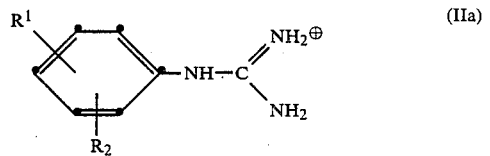

(II$a$)

or the free guanidine base of formula II$b$

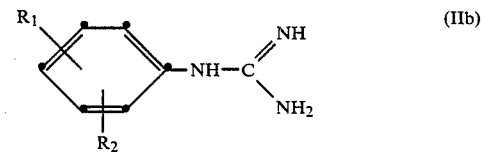

(II$b$)

is reacted with a diketone of formula III

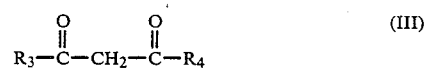

(III)

without solvents or in an aprotic solvent, preferably in a protic solvent, at temperatures of from 60° C. to 160° C., preferably from 60° C. to 110° C.; or 2. in a multi-stage process:
2.1 urea of formula IV

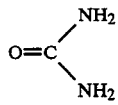

is reacted with a diketone of formula III

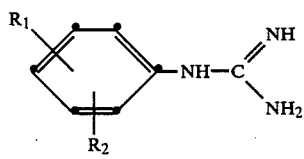

in the presence of an acid in an inert solvent at temperatures of from 20° C. to 140° C., preferably from 20° C. to 40° C., and is cyclised to give a pyrimidine compound of formula V

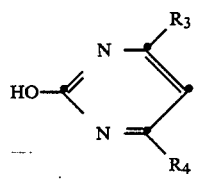

and 2.2 the OH group in the resulting compound of formula V is exchanged for halogen by further reaction with excess POHal$_3$, in the presence or in the absence of a solvent, at temperatures of from 50° C. to 110° C., preferably at the reflux temperature of POHal$_3$, to yield

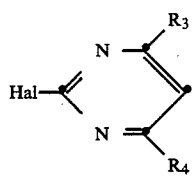

Hal in the above formulae being halogen, especially chlorine or bromine, and 2.3 the resulting compound of formula VI is reacted further with an aniline compound of formula VII

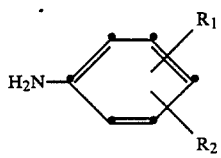

depending on the reaction conditions either (a) in the presence of a proton acceptor, such as an excess of the aniline compound of formula VII or an inorganic base, with or without solvents, or (b) in the presence of an acid in an inert solvent, in each case at temperatures of from 60° C. to 120° C., preferably from 80° C. to 100° C.; or 3. in a two-stage process:
3.1 a guanidine salt of formula VIII

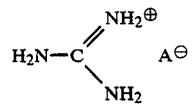

is cyclised with a diketone of formula III

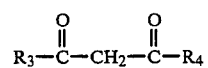

(a) without solvents at temperatures of from 100° C. to 160° C., preferably from 120° C. to 150° C., or (b) in an inert solvent at temperatures of from 30° C. to 140° C., preferably from 60° C. to 120° C., to give a pyrimidine compound of formula IX

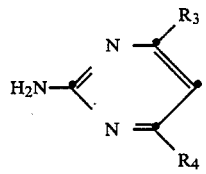

and 3.2 the resulting compound of formula IX is reacted with a compound of formula X $$\underset{R_2}{\underset{|}{Y-\text{\Large{\hexagon}}-R_1}}$$ (X)

in the presence of a proton acceptor in aprotic solvents at temperatures of from 30° C. to 140° C., preferably from 60° C. to 120° C., to remove HY, the substituents R$_1$ to R$_4$ in formulae II to X being as defined for formula I, A$^\ominus$ being an acid anion and Y being halogen; or 4. in a multi-stage process:
4.1(a) thiourea of formula XI $$S=C\overset{NH_2}{\underset{NH_2}{\diagup}}$$ (XI)

is reacted with a diketone of formula III $$R_3-\overset{O}{\overset{\|}{C}}-CH_2-\overset{O}{\overset{\|}{C}}-R_4$$ (III)

in the presence of an acid in an inert solvent at temperatures of from 20° C. to 140° C., preferably from 20° C. to 60° C., and cyclised to give a pyrimidine compound of formula

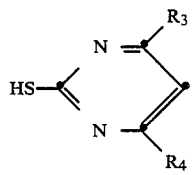

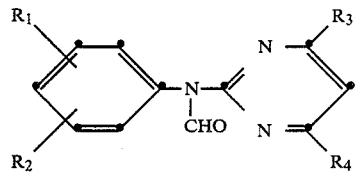

and the alkali metal or alkaline earth metal salt thereof is reacted with a compound of formula XIII

ZR$_5$ (XIII)

wherein R$_5$ is C$_1$–C$_8$alkyl, or benzyl that is unsubstituted or substituted by halogen and/or by C$_1$–C$_4$alkyl and Z is halogen, to give a pyrimidine compound of formula XIV

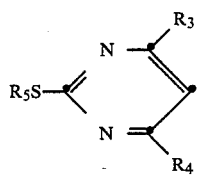

or (b) an isothiuronium salt of formula XV

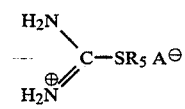

is reacted with a diketone of formula III, preferably in a protic solvent, at temperatures of from 20° C. to 140° C., preferably from 20° C. to 80° C., and a pyrimidine compound of formula XIV is likewise obtained, and 4.2 the resulting compound of formula XIV is oxidised with an oxidising agent, for example with a peracid, to give the pyrimidine compound of formula XVI

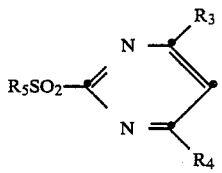

and 4.3 the resulting compound of formula XVI is reacted with a formylaniline of formula XVII

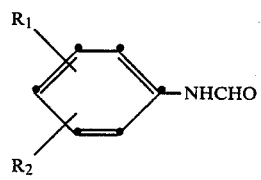

in an inert solvent in the presence of a base as proton acceptor, at temperatures of from −30° C., to 120° C., to give a compound of formula XVIII and 4.4 the resulting compound of formula XVIII is subjected to hydrolysis in the presence of a base, for example an alkali metal hydroxide, or of an acid, for example a hydrohalic acid or sulfuric acid, in water or aqueous solvent mixtures, such as aqueous alcohols or dimethylformamide, at temperatures of from 10° C. to 110° C., preferably from 30° C. to 60° C., the substituents R$_1$ to R$_4$ in formulae XI to XVIII being as defined for formula I and A$^\ominus$ being an acid anion and Y being halogen.

Compounds of formula I in which R$_3$ is the CH$_2$OH group can be prepared by special processes, as follows:

A1.1 the guanidine salt of formula IIa

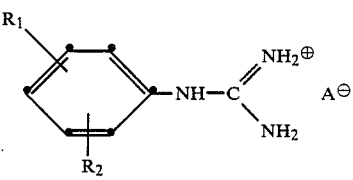

or the guanidine of formula IIb

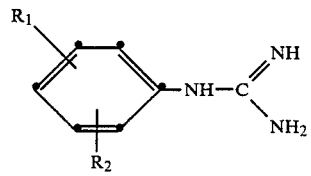

is reacted with a ketone of formula XIX

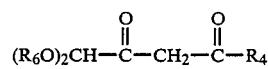

in which R$_6$ is C$_1$–C$_4$alkyl, in a protic solvent or without solvents, at temperatures of from 40° C. to 160° C., preferably from 60° C. to 110° C., to give a pyrimidine compound of formula XX

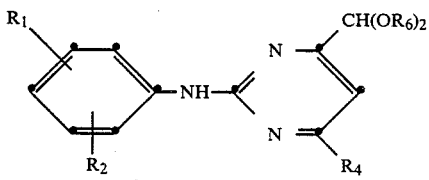

and

A1.2 the resulting acetal of formula XX is hydrolysed in the presence of an acid, for example a hydrohalic acid or sulfuric acid, in water or aqueous solvent mixtures, for example with solvents such as alcohols or dimethylformamide, at temperatures of from 20° C. to 100° C., preferably from 30° C. to 60° C., to give the pyrimidinealdehyde of formula XXI

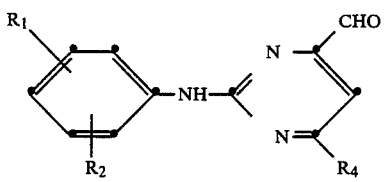

and

A1.3 the resulting compound of formula XXI is hydrogenated with elemental hydrogen using a catalyst or is reduced with a reducing agent, such as sodium borohydride, to give the corresponding alcohol XXII

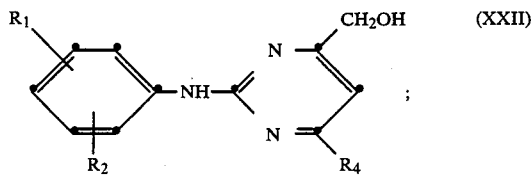

or

A2.1 the guanidine salt of formula IIa or the guanidine of formula IIb is reacted with a diketone of formula XXIII

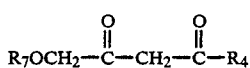

in which $R_7$ is benzyl that is unsubstituted or substituted by halogen or by $C_1$-$C_4$alkyl, in a protic solvent or without solvents, at temperatures of from 40° C. to 160° C., preferably from 60° C. to 110° C., to give a pyrimidine compound of formula XXIV

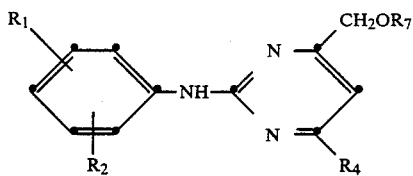

and in that compound

A2.2 the $CH_2OR_7$ radical is converted into a $CH_2OH$ radical by hydrogenation in a solvent, preferably an aprotic solvent, for example dioxane or tetrahydrofuran, with a catalyst, such as palladium-on-carbon, preferably Raney nickel, at temperatures of from 20° C. to 90° C., preferably from 50° C. to 90° C.; or A3.1 the guanidine salt of formula IIa or the guanidine of formula IIb is reacted with a diketone of formula XXV

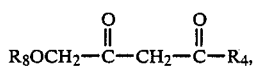

in which R8 is $C_1$-$C_6$alkyl, $C_3$-$C_6$alkenyl or benzyl that is unsubstituted or substituted by halogen or by $C_1$-$C_4$alkyl, in a protic solvent or without solvents, at temperatures of from 40° C. to 160° C., preferably from 60° C. to 110° C., to give a pyrimidine compound XXVI

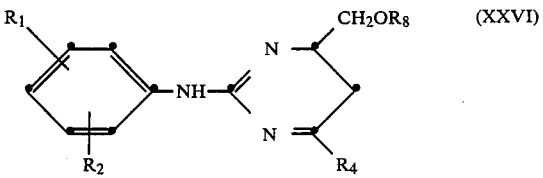

and

A3.2 with the resulting compound of formula XXVI an ether cleavage is carried out with a hydrohalic acid, preferably hydrobromic acid, or a Lewis acid, such as aluminium halide (for example $AlCl_3$) or boron halide $B(Hal)_3$ (for example $BBr_3$ or $BCl_3$), in aprotic solvents, for example hydrocarbons or halogenated hydrocarbons, at temperatures of from −80° C. to 30° C., preferably from −70° C. to 20° C.

Compounds of formula I in which $R_3$ is the $CH_2Hal$ group can be prepared by reacting a compound of formula XXII with phosphorus halide or thionyl halide in the presence of tertiary bases, for example pyridine or triethylamine, in inert solvents, at temperatures of from 0° C. to 110° C., preferably from 0° C. to 80° C.

Compounds of formula I in which $R_3$ is the $CH_2F$ group can be prepared by reacting a compound of formula XXVII

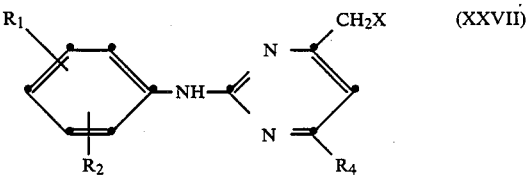

in which X is chlorine or bromine, with potassium fluoride, preferably lyophilised potassium fluoride, in the presence of catalytic amounts of cesium fluoride or a Crown ether, for example 18-Crown-6-ether, in aprotic solvents, such as acetonitrile, at temperatures of from 50° C. to 160° C. in a pressure autoclave.

A further process for the preparation of compounds of formula I in which $R_3$ is the $CH_2F$ group consists in fluorinating a compound of formula XXII with N,N-diethylaminosulfur trifluoride (=DAST) in aprotic solvents, such as dichloromethane, chloroform, tetrahydrofuran or dioxane, at temperatures of from 0° C. to 100° C., preferably from 10° C. to 50° C.

In the above formulae XVIII to XXVII too, $R_1$, $R_2$ and $R_4$ are as defined for formula I.

In the described processes, in compounds of formulae IIa and VIII the following salt radicals, for example, are suitable for the acid anion $A^\ominus$: carbonate, hydrogen carbonate, nitrate, halide, sulfate and hydrogen sulfate.

In the processes described above, in the compound of formula XV the following salts, for example, are suitable for the acid anion $A^\ominus$: halide, sulfate and hydrogen sulfate.

Halide in each case is to be understood as meaning fluoride, chloride, bromide or iodide, preferably bromide or chloride.

The acids used are especially inorganic acids, such as, for example, hydrohalic acids, for example hydrofluoric acid, hydrochloric acid or hydrobromic acid, and also sulfuric acid, phosphoric acid or nitric acid; however, suitable organic acids may also be used, such as, inter alia, acetic acid and toluenesulfonic acid.

As proton acceptors there are used, for example, inorganic or organic bases, such as, for example, alkali metal or alkaline earth metal compounds, for example the hydroxides, oxides or carbonates of lithium, sodium, potassium, magnesium, calcium, strontium and barium, or also hydrides, such as, for example, sodium hydride. As organic bases there may be mentioned, for example, tertiary amines, such as triethylamine, triethylenediamine, pyridine.

In the processes described above, for example, the following solvents may be used, dependent on the particular reaction conditions, in addition to those already mentioned:

Halogenated hydrocarbons, especially chlorinated hydrocarbons, such as tetrachloroethylene, tetrachloroethane, dichloropropane, methylene chloride, dichlorobutane, chloroform, chloronaphthalene, carbon tetrachloride, trichloroethane, trichloroethylene, pentachloroethane, difluorobenzene. 1,2-dichloroethane, 1,1-dichloroethane, 1,2-cis-dichloroethylene, chlorobenzene, fluorobenzene, bromobenzene, dichlorobenzene, dibromobenzene, chlorotoluene, trichlorotoluene; ethers, such as ethyl propyl ether, methyl tert.-butyl ether, n-butyl ethyl ether, di-n-butyl ether, diisobutyl ether, diisoamyl ether, diisopropyl ether, anisole, cyclohexyl methyl ether, diethyl ether, ethylene glycol dimethyl ether, tetrahydrofuran, dioxane, thioanisole, dichlorodiethyl ether; nitrohydrocarbons, such as nitromethane, nitroethane, nitrobenzene, chloronitrobenzene, o-nitrotoluene; nitriles, such as acetonitrile, butyronitrile, isobutyronitrile, benzonitrile, m-chlorobenzonitrile; aliphatic or cycloaliphatic hydrocarbons, such as heptane, hexane, octane, nonane, cymol, petroleum fractions within a boiling point range of from 70° C. to 190° C., cyclohexane, methylcyclohexane, decalin, petroleum ether, ligroin, trimethylpentane, such as 2,3,3-trimethylpentane; esters, such as ethyl acetate, ethyl acetoacetate, isobutyl acetate; amides, for example formamide, methylformamide, dimethylformamide; ketones, such as acetone, methyl ethyl ketone; alcohols, especially lower aliphatic alcohols, such as, for example, methanol, ethanol, n-propanol, isopropanol and the butanol isomers; and, where appropriate, also water. Also suitable are mixtures of the mentioned solvents and diluents.

Methods of synthesis that are analogous to the above-described preparation processes have been published in the literature.

As references there may be mentioned:

Process 1: A. Kreutzberger and J. Gillessen, J. Heterocyclic Chem. 22, 101 (1985).

Process 2:, Stage 2.1: O. Stark, Ber. Dtsch. Chem. Ges. 42,699 (1909); J. Hale, J. Am. Chem. Soc. 36, 104 (1914); G. M. Kosolapoff, J. Org. Chem. 26, 1895 (1961). Stage 2.2: St. Angerstein, Ber. Dtsch. Chem. Ges. 34, 3956 (1901); G. M. Kosolapoff, J. Org. Chem. 26, 1895 (1961). Stage 2.3: M. P. V. Boarland and J. F. W. McOmie, J. Chem. Soc. 1951, 1218; T. Matsukawa and K. Shirakuwa, J. Pharm. Soc. Japan 71, 933 (1951); Chem. Abstr. 46, 4549 (1952).

Process 3: A. Combes and C. Combes, Bull. Soc. Chem. (3), 7, 791 (1892); W. J. Hale and F. C. Vibrans, J. Am. Chem. Soc. 40, 1046 (1918).

The described preparation processes, including all partial steps, form part of the present invention.

The following compounds, which are used as intermediates in the preparation of the compounds of formula I, are novel and form part of the present invention:

(1) Compounds of formula

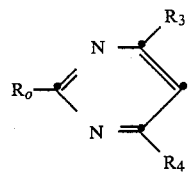

in which:

$R_o$ is halogen or $R_5SO_2$; $R_3$ is hydrogen; $C_1$–$C_4$alkyl; or $C_1$–$C_4$alkyl substituted by halogen, hydroxy and/or cyano; cyclopropyl; or cyclopropyl mono- to tri-substituted by methyl and/or by halogen; $R_4$ is $C_3$–$C_6$cycloalkyl or $C_3$–$C_6$cycloalkyl mono- to tri-substituted by methyl and/or by halogen; and $R_5$ is $C_1$–$C_8$alkyl or benzyl that is unsubstituted or substituted by halogen and/or by $C_1$–$C_4$alkyl. Chlorine and bromine are preferred as halogen substituent $R_o$.

(2) Compounds of formula XXI

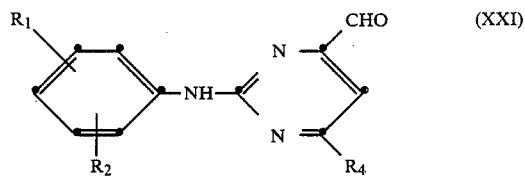

in which:

$R_1$ and $R_2$ independently of one another are hydrogen, halogen, $C_1$–$C_3$alkyl, $C_1$–$C_2$haloalkyl, $C_1$–$C_3$alkoxy or $C_1$–$C_3$haloalkoxy; and $R_4$ is $C_3$–$C_6$cycloalkyl or $C_3$–$C_6$cycloalkyl mono-to tri-substituted by methyl and/or by halogen.

Surprisingly, it has been found that the compounds of formula I have, for practical field application purposes, a very advantageous biocidal spectrum against insects and phytopathogenic microorganisms, especially fungi. Compounds of formula I have very advantageous curative, preventive and, in particular, systemic properties, and can be used for protecting numerous cultivated plants. With the compounds of formula I it is possible to inhibit or destroy the pests which occur in plants or in parts of plants (fruit, blossoms, leaves, stems, tubers, roots) in different crops of useful plants, while at the same time the parts of plants which grow later are also protected, for example, from attack by phytopathogenic microorganisms.

The compounds of formula I are effective, for example, against the phytopathogenic fungi belonging to the following classes: Fungi imperfecti (especially Botrytis, and also Pyricularia, Helminthosporium, Fusarium, Septoria, Cercospora and Alternaria); Basidiomycetes (e.g. Rhizoctonia, Hemileia, Puccinia). They are also effective against the class of the Ascomycetes (e.g. Venturia and Erysiphe, Podosphaera, Monilinia, Uncinula) and of the Oomycetes (e.g. Phytophthora, Pythium, Plasmopara). The compounds of formula I can also be used as dressing agents for protecting seeds (fruit, tubers, grains) and plant cuttings against fungus infections as well as against phytopathogenic fungi which occur in the soil. In addition, compounds of formula I are effective against insect pests, for example against pests on cereals such as rice.

The invention also relates to compositions containing as active ingredient compounds of formula I, especially plant-protecting compositions, and to their use in the agricultural sector or related fields.

The present invention further embraces the preparation of those compositions, which comprises homogeneously mixing the active ingredient with one or more compounds or groups of compounds described herein. The invention furthermore relates to a method of treating plants, which comprises applying thereto the novel compounds of formula I or the novel compositions.

Target crops to be protected within the scope of the present invention comprise e.g. the following species of plants: cereals (wheat, barley, rye, oats, rice, maize, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as tobacco, nuts, coffee, sugar cane, tea, pepper, vines, hops, bananas and natural rubber plants, as well as ornamentals.

The compounds of formula I are normally applied in the form of compositions and can be applied to the crop area or plant to be treated, simultaneously or in succession, with further active substances. These active substances can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The number of applications and the rate of application depend on the risk of infestation by the corresponding pathogen. However, the compounds of formula I can also penetrate the plant through the roots via the soil (systemic action) if the locus of the plant is impregnated with a liquid formulation, or if the compounds are applied in solid form to the soil, e.g. in granular form (soil application). In paddy rice crops, such granulates may be applied in metered amounts to the flooded rice field. The compounds of formula I may, however, also be applied to seeds (coating) either by impregnating the seeds with a liquid formulation containing a compound of formula I, or coating them with a solid formulation.

The compounds of formula I are used in unmodified form or, preferably, together with the adjuvants conventionally employed in the art of formulation, and are for this purpose advantageously formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic nature can be used, e.g. especially dolomite or pulverised plant residues.

Particularly advantageous application-promoting adjuvants which are able to reduce substantially the rate of application are also natural (animal or vegetable) or synthetic phospholipids of the series of the cephalins and lecithins, which can be obtained e.g. from soybeans.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyllaurin salts.

More frequently, however, so-called synthetic surfactants are used, especially alkanesulfonates, fatty alcohol sulfates, sulfonated benzimidazole derivatives or alkylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ammonium bromide.

Further surfactants customarily employed in the art of formulation are known to the person skilled in the art or can be taken from the relevant specialist literature.

The agrochemical compositions usually contain 0.1 to 99%, preferably 0.1 to 95%, of a compound of formula I, 99.9 to 1%, preferably 99.9 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

The following Examples serve to illustrate the invention in greater detail, without limiting it.

1. PREPARATION EXAMPLES

Example 1.1

Preparation of 2-phenylamino-4-methyl-6-cyclopropylpyrimidine

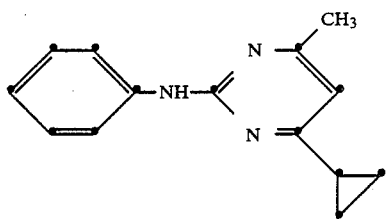

[Comp. no. 1.1]

10 g (51 mmol) of phenylguanidine hydrogen carbonate and 9.7 g (77 mmol) of 1-cyclopropyl-1,3-butanedione are heated at 110° C. for 6 hours with stirring, the evolution of carbon dioxide which occurs subsiding as the reaction progresses. After the dark brown emulsion has been cooled to room temperature, 50 ml of diethyl ether are added and the mixture is washed twice with 20 ml of water each time, dried over sodium sulfate and filtered, and the solvent is evaporated. The dark brown oil which remains (=13.1 g) is purified by column chromatography over silica gel (diethyl ether/toluene: 5/3). After the eluant mixture has been evaporated off, the brown oil is made to crystallise and recrystallised from diethyl ether/petroleum ether at 30°–50° C. Light-brown crystals are obtained. Melting point: 67°–69° C.; yield: 8.55 g (38 mmol) (=74.5% of the theoretical yield).

Example 1.2

Preparation of 2-anilino-4-formyldiethyl-acetal-6-cyclopropylpyrimidine

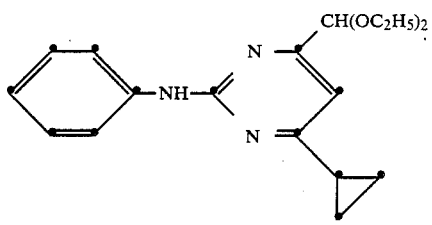

11.7 g (59.2 mmol) of phenylguanidine hydrogen carbonate and 13.3 g (62.2 mmol) of 1-cyclopropyl-3-formyldiethylacetal-1,3-propanedione in 40 ml of ethanol are heated under reflux for 5 hours with stirring, the evolution of carbon dioxide subsiding as the reaction progresses. After the dark brown emulsion has been cooled to room temperature, 80 ml of diethyl ether are added and the mixture is washed twice with 30 ml of water each time, dried over sodium sulfate and filtered, and the solvent is evaporated. The dark brown oil which remains (17 g) is purified by column chromatography over silica gel (toluene/ethyl acetate: 5/2). After the eluant mixture has been evaporated off, a reddish brown oil remains which has a refractive index $n_D^{25}$:1.5815. Yield: 15 g (48 mmol; 81.1% of the theoretical yield).

Example 1.3

Preparation of
2-anilino-4formyl-6-cyclo-propylpyrimidine

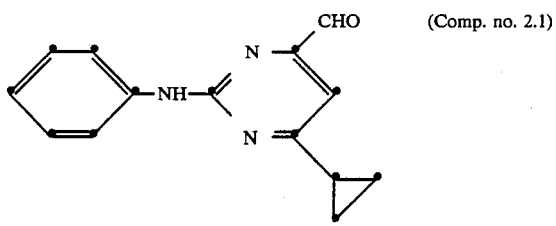
(Comp. no. 2.1)

12.3 g (39.3 mmol) of 2-anilino-4-formyldiethylacetal-6-cyclopropylpyrimidine, 4 g (39.3 mmol) of concentrated hydrochloric acid and 75 ml of water are heated at 50° C. for 14 hours with vigorous stirring and, after the addition of 2 g (19.6 mmol) of concentrated hydrochloric acid, stirring is continued for a further 24 hours at that temperature. After the beige-coloured suspension has been cooled to room temperature, 50 ml of ethyl acetate are added thereto and the mixture is rendered neutral with 7 ml of 30% sodium hydroxide solution. The ethyl acetate solution is then separated off, dried over sodium sulfate and filtered, and the solvent is evaporated. For purification, the brownish solid is recrystallised from 20 ml of isopropanol in the presence of active carbon. The yellowish crystals melt at 112°–114° C. Yield: 7.9 g (33 mmol; 84% of the theoretical yield).

Example 1.4

Preparation of
2-anilino-4-hydroxymethyl-6-cyclopropylpyrimidine

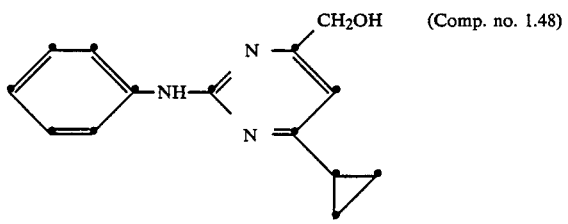
(Comp. no. 1.48)

(a) 2.3 g (60 mmol) of sodium borohydride are added in portions at room temperature, within a period of 15 minutes, with stirring, to 14.1 g (59 mmol) of 2-anilino-4-formyl-6-cyclopropylpyrimidine in 350 ml of absolute methanol, whereupon the reaction mixture warms up to 28° C. with evolution of hydrogen. After 4 hours the mixture is acidified by the dropwise addition of 10 ml of concentrated hydrochloric acid, 120 ml of 10% sodium hydrogen carbonate solution are added dropwise, and the mixture is then diluted with 250 ml of water. The resulting precipitate is filtered off, dried, largely dissolved in 600 ml of diethyl ether at elevated temperature, treated with active carbon and filtered. The clear filtrate is concentrated until it becomes turbid and is then diluted with petroleum ether, and the light-yellow crystalline powder is filtered off; m.p. 123°–125° C. Yield: 10.8 g (44.8 mmol; 75.9% of the theoretical yield).

(b) 5.9 g (23 mmol) of 2-anilino-4-methoxymethyl-6-cyclopropylpyrimidine, prepared from phenylguanidine and 1-cyclopropyl-4-methoxy-1,3-butanedione, are dissolved in 200 ml of dichloromethane and the solution is cooled to −68° C. 6.8 g (27 mmol) of boron tribromide are slowly added dropwise to the salmon-coloured solution within a period of half an hour, with vigorous stirring, and the cooling bath is then removed and stirring is continued for a further 2 hours at room temperature. After the addition of 150 g of ice-water, the precipitated crude product is filtered off and recrystallised from methanol using active carbon. The light-yellow crystals melt at 124°–126° C. Yield: 4.7 g (19.5 mmol; 84.7% of the theoretical yield).

Example 1.5

Preparation of
2-phenylamino-4-bromomethyl-6-cyclopropylpyrimidine

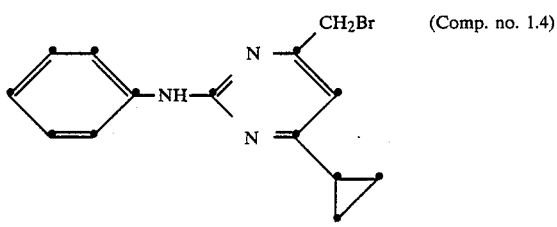
(Comp. no. 1.4)

15.6 g (75 mmol) of thionyl bromide in 50 ml of diethyl ether are added dropwise within a period of half an hour, with stirring, to 12 g (50 mmol) of 2-phenylamino-4-hydroxymethyl-6-cyclopropylpyrimidine and 0.4 g (50 mmol) of pyridine in 350 ml of diethyl ether. After stirring for 2 hours at room temperature, a further 0.4 g (50 mmol) of pyridine are added and the mixture is heated under reflux for 5 hours. After cooling to room temperature, 200 ml of water are added and the pH is adjusted to 7 by the dropwise addition of 140 ml of saturated sodium hydrogen carbonate solution. The diethyl ether phase is separated off and then washed twice with 100 ml of water each time, dried over sodium sulfate and filtered, and the solvent is evaporated. The brown oil which remains is purified by column chromatography over silica gel (toluene/chloroform/diethyl ether/petroleum ether (b.p. 50°–70° C.): 5/3/1/1). After the eluant mixture has been evaporated off, the yellow oil is diluted with diethyl ether/petroleum ether (b.p. 50°–70° C.) and crystallised at reduced temperature. The yellow crystalline powder melts at 77.5°–79.5° C. Yield: 9.7 g (32 mmol; 64% of the theoretical yield).

Example 1.6

Preparation of
2-phenylamino-4-fluoromethyl-6-cyclopropylpyrimidine

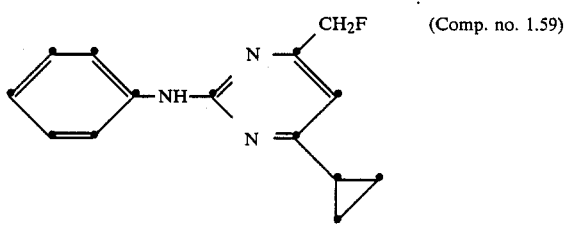
(Comp. no. 1.59)

(a) 3.9 g (12.8 mmol) of 2-phenylamino-4-bromomethyl-6-cyclopropylpyrimidine, 1.5 g (26 mmol) of spray-dried potassium fluoride and 0.3 g (1.13 mmol) of 18-Crown-6-ether are heated under reflux for 40 hours in 50 ml of acetonitrile. A further 0.75 g (13 mmol) of potassium fluoride is then added and the mixture is heated for 22 hours. To complete the reaction, a further 0.75 g (13 mmol) of spray-dried potassium fluoride and 0.1 g (0.38 mmol) of 18-Crown-6-ether are added and the mixture is heated under reflux for a further 24 hours. After the suspension has been cooled to room temperature, 150 ml of diethyl ether are added and the mixture is washed three times with 20 ml of water each time, dried over sodium sulfate and filtered, and the solvent is evaporated. The brown oil which remains is purified by column chromatography over silica gel (toluene/chloroform/diethyl ether/petroleum ether (b.p. 50°–70° C.): 5/3/1/1). After the eluant mixture has been evaporated off, the yellow oil is diluted with 10 ml of petroleum ether (b.p. 50°–70° C.) and crystallised at reduced temperature. The yellow crystals melt at 48°–52° C.; yield: 2.1 g (8.6 mmol); 67.5% of the theoretical yield.

(b) 6.1 g (37.8 mmol) of diethylaminosulfur trifluoride in 15 ml of dichloromethane are slowly added dropwise within a period of one hour, with stirring, to a suspension of 9.1 g (37.8 mmol) of 2-phenylamino-4-hydroxymethyl-6-cyclopropylpyrimidine in 80 ml of dichloromethane. After the addition of 50 ml of ice-water, 50 ml of 10% aqueous sodium hydrogen carbonate solution are added dropwise. When the evolution of carbon dioxide has ceased, the organic phase is separated off and the aqueous phase is extracted twice with 20 ml of dichloromethane each time. The combined dichloromethane solutions are washed with 15 ml of water, dried over sodium sulfate and filtered, and the solvent is evaporated. The black oil which remains is purified by column chromatography over silica gel (toluene/chloroform/diethyl ether/petroleum ether (b.p. 50°–70° C.); 5/3/1/1). After the eluant mixture has been evaporated off, the yellow oil is diluted with 20 ml of petroleum ether (b.p. 50°–70° C.) and crystallised at reduced temperature. The yellowish crystals melt at 50°–52° C. Yield: 4.9 g (20.1 mmol; 53% of the theoretical yield).

Example 1.7

Preparation of 2-hydroxy-4-methyl-6-cyclo-propylpyrimidine

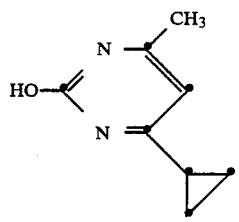

15 ml of concentrated hydrochloric acid are added at room temperature to 6 g (100 mmol) of urea and 12.6 g (100 mmol) of 1-cyclopropyl-1,3-butanedione in 35 ml of ethanol. After the mixture has stood for 10 days at room temperature, it is concentrated in a rotary evaporator at a bath temperature not exceeding 45° C. The residue is dissolved in 20 ml of ethanol, the hydrochloride of the reaction product precipitating after a short time. 20 ml of diethyl ether are added with stirring, and the precipitated white crystals are filtered off, washed with an ethanol/diethyl ether mixture and dried. Concentration of the filtrate and recrystallisation from an ethanol/diethyl ether mixture: ½ yield a further quantity of hydrochloride. The white crystals melt >230° C.

Yield: hydrochloride 12.6 g (67.5 mmol; 67.5% of the theoretical yield).

Example 1.8

Preparation of 2-chloro-4-methyl-6-cyclo-propylpyrimidine

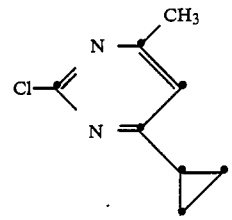

(Comp. no. 3.1)

52.8 g (0.24 mol) of 2-hydroxy-4-methyl-6-cyclopropylpyrimidine hydrochloride are introduced at room temperature, with stirring, into a mixture of 100 ml (1.1 mol) of phosphorus oxychloride and 117 g (0.79 mol) of diethylaniline, the temperature rising to 63° C. After the mixture has been heated for 2 hours at 110°, it is cooled to room temperature and transferred onto an ice-water/methylene chloride mixture, with stirring. The organic phase is separated off and washed with saturated aqueous sodium hydrogen carbonate solution until neutral. Removal of the solvent by evaporation yields 116.4 g of oil, which is composed of the reaction product and diethylaniline. Separation of the diethylaniline and purification of the crude reaction product are effected by column chromatography over silica gel (hexane/diethyl acetate: 3/1). The colourless oil which crystallises after several days has a refractive index $n_D^{25}$: 1.5419; yield: 35.7 g (0.21 mol; 87.5% of the theoretical yield); melting point: 33°–34° C.

Example 1.9

Preparation of 2-(m-fluorophenylamino)-4-methyl-6-cyclopropylpyrimidine

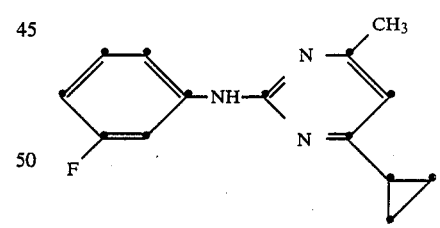

(Comp. no. 1.63)

A solution of 5.5 g (50 mmol) of 3-fluoroaniline and 9.3 g (55 mmol) of 2-chloro-4-methyl-6-cyclopropylpyrimidine in 100 ml of ethanol is adjusted to pH 1 with 5 ml of concentrated hydrochloric acid with stirring, and is then heated under reflux for 18 hours. After the brown emulsion has been cooled to room temperature, it is rendered alkaline with 10 ml of 30% ammonia, poured onto 100 ml of ice-water and extracted twice with 150 ml of diethyl ether each time. The combined extracts are washed with 50 ml of water, dried over sodium sulfate and filtered, and the solvent is evaporated. The yellowish crystals which remain are purified by recrystallisation from diisopropyl ether/petroleum ether (b.p. 50°–70° C.). The white crystals melt at 87°–89° C.; yield: 8.3 g (34 mmol; 68% of the theoretical yield).

The following compounds of formula I can be prepared in this manner or by one of the methods described hereinbefore.

TABLE 1

Compounds of the formula

[Structure: R1, R2-substituted phenyl-NH-C(CH3)=N-... with R3, R4 substituents]

| Comp. no. | $R_1$ | $R_2$ | $R_3$ | $R_4$ | Physical constant |
|---|---|---|---|---|---|
| 1.1 | H | H | $CH_3$ | cyclopropyl | m.p. 67–69° C. |
| 1.2 | 2-Cl | H | $CH_3$ | cyclopropyl | |
| 1.3 | H | H | H | cyclopropyl | m.p. 53–56° C. |
| 1.4 | H | H | $-CH_2Br$ | cyclopropyl | m.p. 77,5–79,5° C. |
| 1.5 | 3-Cl | H | $CH_3$ | cyclopropyl | m.p. 104–105° C. |
| 1.6 | H | H | $-C_2H_5$ | cyclopropyl | m.p. 42–45° C. |
| 1.7 | 4-Cl | H | $-CH_3$ | cyclopropyl | m.p. 86–87° C. |
| 1.8 | H | H | $-CH_2Br$ | 1-methylcyclopropyl | |
| 1.9 | H | H | $-CH_2Cl$ | 1-methylcyclopropyl | m.p. 50–52° C. |
| 1.10 | 4-$CH_3$ | H | $-CH_3$ | cyclopropyl | m.p. 53–56° C. |

TABLE 1-continued
Compounds of the formula
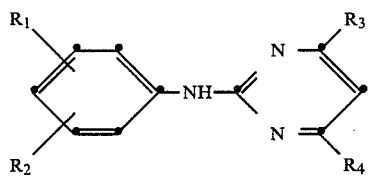
| Comp. no. | $R_1$ | $R_2$ | $R_3$ | $R_4$ | Physical constant |
|---|---|---|---|---|---|
| 1.11 | H | H | —CF$_3$ | 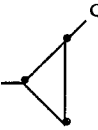 | |
| 1.12 | H | H | —C$_3$H$_7$-n | 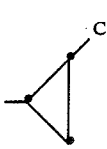 | m.p. 44–46° C. |
| 1.13 | H | H | —CH$_2$OH | 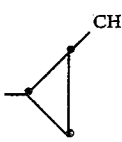 | m.p. 111–113° C. |
| 1.14 | H | H | —CH$_3$ | 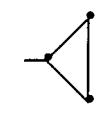 | m.p. 73–74° C. |
| 1.15 | 4-OCH$_3$ | H | CH$_3$ | 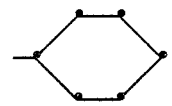 | m.p. 48–50° C. |
| 1.16 | H | H | —CH$_2$CH$_2$OH | 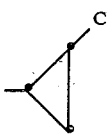 | |
| 1.17 | H | H | —CH$_2$Br |  | |
| 1.18 | H | H | —C$_4$H$_9$-n | 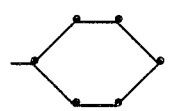 | dark brown oil $n_D^{24}$: 1.5992 |
| 1.19 | H | H | —CH$_2$OH |  | |
| 1.20 | 4-OC$_2$H$_5$ | H | CH$_3$ | | m.p. 33–36° C. |

TABLE 1-continued
Compounds of the formula
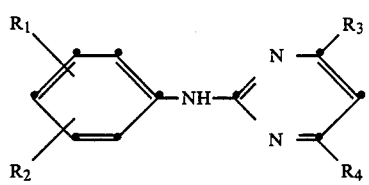
| Comp. no. | R₁ | R₂ | R₃ | R₄ | Physical constant |
|---|---|---|---|---|---|
| 1.21 | H | H | H | cyclopropyl with CH₃ | |
| 1.22 | H | H | —CH₂Br | cyclopentyl | |
| 1.23 | H | H | —CH₂Br | cyclohexyl | |
| 1.24 | H | H | H | cyclobutyl | |
| 1.25 | H | H | —C₄H₉ sek. | cyclopropyl | oil $n_D^{24}$: 1.6002 |
| 1.26 | H | H | —CH₂OH | cyclopropyl with CH₃ | |
| 1.27 | 4-Br | H | —CH₃ | cyclopropyl | m.p. 94–95° C. |
| 1.28 | H | H | —CH₃ | cyclohexyl | m.p. 97–98° C. |
| 1.29 | H | H | —CF₃ | cyclohexyl | |
| 1.30 | H | H | —C₄H₉ tert. | cyclopropyl | |
| 1.31 | H | H | —CH₃ | cyclobutyl | m.p. 50–52° C. |

TABLE 1-continued

Compounds of the formula

R_1, R_2-phenyl-NH-C(R_3)=N-... pyrimidine ring with R_3, R_4

| Comp. no. | $R_1$ | $R_2$ | $R_3$ | $R_4$ | Physical constant |
|---|---|---|---|---|---|
| 1.32 | H | H | —CF₃ | 1-methylcyclopropyl | |
| 1.33 | 4-F | H | —CH₃ | cyclopropyl | m.p. 89–91° C. |
| 1.34 | H | H | H | cyclohexyl | |
| 1.35 | H | H | —CH₂Cl | cyclopropyl | m.p. 55–57° C. |
| 1.36 | H | H | —CF₃ | cyclobutyl | |
| 1.37 | 4-OCHF₂ | H | —CH₃ | cyclopropyl | oil $n_D^{25}$: 1.5763 |
| 1.38 | H | H | —C₂H₅ | 1-methylcyclopropyl | |
| 1.39 | H | H | —CHCl₂ | cyclopropyl | m.p. 56–58° C. |
| 1.40 | 3-Cl | 5-Cl | —CH₃ | cyclopropyl | |
| 1.41 | H | H | —CHCl₂ | cyclopentyl | |
| 1.42 | H | H | —CH₃ | 1-methylcyclopropyl | m.p. 63–65° C. |

TABLE 1-continued

Compounds of the formula

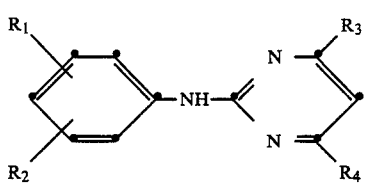

| Comp. no. | R₁ | R₂ | R₃ | R₄ | Physical constant |
|---|---|---|---|---|---|
| 1.43 | H | H | —CH$_2$OH | (cyclobutyl) | |
| 1.44 | 3-OC$_2$H$_5$ | 4-OC$_2$H$_5$ | —CH$_3$ | (cyclopropyl) | oil $n_D^{25}$ 1.5498 |
| 1.45 | H | H | —CF$_3$ | (cyclopropyl) | m.p. 66–69° C. |
| 1.46 | 4-OCF$_3$ | H | —CH$_3$ | (cyclopropyl) | |
| 1.47 | H | H | —CH$_2$OH | (cyclobutyl) | |
| 1.48 | H | H | —CH$_2$OH | (cyclopropyl) | m.p. 123–125° C. |
| 1.49 | 3-CF$_3$ | 4-Cl | —CH$_3$ | (cyclopropyl) | m.p. 128–130° C. |
| 1.50 | H | H | H | (cyclobutyl) | |
| 1.51 | H | H | H | (1-methylcyclopropyl) | |
| 1.52 | H | H | —CH$_2$CH$_2$OH | (cyclopropyl) | |
| 1.53 | 3-Cl | 4-Cl | —CH$_3$ | (cyclopropyl) | m.p. 85–87° C. |

TABLE 1-continued
Compounds of the formula
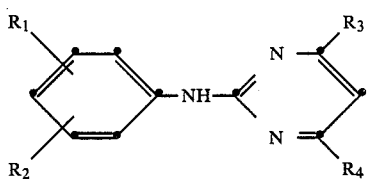
| Comp. no. | R₁ | R₂ | R₃ | R₄ | Physical constant |
|---|---|---|---|---|---|
| 1.54 | H | H | —CH₃ | (F-cyclopropyl) | m.p. 73–74° C. |
| 1.55 | 2-F | H | —CH₃ | (cyclopropyl) | |
| 1.56 | H | H | —CH₃ | (Br, CH₃-cyclopropyl) | |
| 1.57 | H | H | H | (F-cyclopropyl) | |
| 1.58 | H | H | —CH₃ | (Cl-cyclopropyl) | m.p. 58–61° C. |
| 1.59 | H | H | —CH₂F | (cyclopropyl) | m.p. 48–52° C. |
| 1.60 | 3-Cl | 4-CH₃ | —CH₃ | (cyclopropyl) | |
| 1.61 | H | H | H | (Cl-cyclopropyl) | |
| 1.62 | H | H | —CH₃ | (Br-cyclopropyl) | |
| 1.63 | 3-F | H | —CH₃ | (cyclopropyl) | m.p. 87–89° C. |
| 1.64 | H | H | —CH₃ | (Cl, CH₃, CH₃-cyclopropyl) | |

TABLE 1-continued
Compounds of the formula
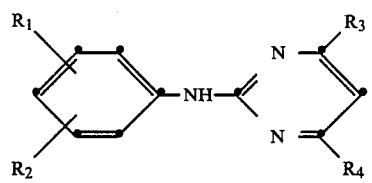
| Comp. no. | $R_1$ | $R_2$ | $R_3$ | $R_4$ | Physical constant |
|---|---|---|---|---|---|
| 1.65 | 2-CH$_3$ | 3-Cl | —CH$_3$ | cyclopropyl | |
| 1.66 | H | H | —CH$_3$ | 2-F-cyclopropyl | m.p. 81–84° C. |
| 1.67 | H | H | —CH$_2$F | 2-F-cyclopropyl | m.p. 63–65° C. |
| 1.68 | 2-Cl | 5-CH$_3$ | —CH$_3$ | cyclopropyl | |
| 1.69 | H | H | —CH$_3$ | 2-Cl-cyclopropyl | m.p. 67–69° C. |
| 1.70 | 2-Br | H | —CH$_3$ | cyclopropyl | |
| 1.71 | 2-CH$_3$ | 4-Cl | —CH$_3$ | cyclopropyl | |
| 1.72 | H | H | —CH$_3$ | cyclobutyl | m.p. 64–66° C. |
| 1.73 | 2-Cl | 6-CH$_3$ | —CH$_3$ | cyclopropyl | |
| 1.74 | H | H | —CH$_2$F | 2-Cl-cyclopropyl | m.p. 43–45° C. |

TABLE 1-continued
Compounds of the formula
| Comp. no. | R₁ | R₂ | R₃ | R₄ | Physical constant |
|---|---|---|---|---|---|
| 1.75 | H | H | —CH$_2$F |  | |
| 1.76 | 3-Br | H | —CH$_3$ |  | |
| 1.77 | H | H |  | 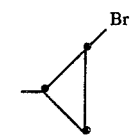 | |
| 1.78 | H | H | —CH$_3$ |  | m.p. 51–53° C. |
| 1.79 | 2-Cl | 4-CH$_3$ | —CH$_3$ |  | |
| 1.80 | H | H | 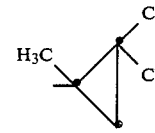 | 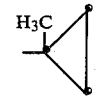 | oil n$_D^{24}$: 1.6101 |
| 1.81 | H | H | —CH$_2$F | 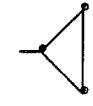 | |
| 1.82 | 3-Cl | 4-F | —CH$_3$ | | |
| 1.83 | H | H | —C$_3$H$_7$-i | 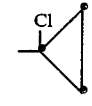 | |
| 1.84 | H | H | —CH$_3$ | 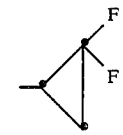 | m.p. 81–84° C. |

TABLE 1-continued
Compounds of the formula
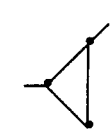
| Comp. no. | R1 | R2 | R3 | R4 | Physical constant |
|---|---|---|---|---|---|
| 1.85 | H | H | —$C_3H_7$-i | 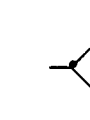 | |
| 1.86 | 4-J | H | —$CH_3$ |  | |
| 1.87 | H | H | —$CH_2F$ | 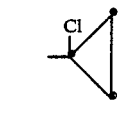 | m.p. 63–65° C. |
| 1.88 | H | H | —$C_4H_9$-n | 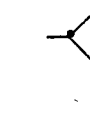 | |
| 1.89 | 2-$CH_3$ | H | —$CH_3$ | 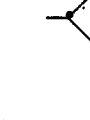 | |
| 1.90 | H | H | —$C_3H_7$-i | 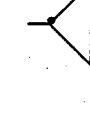 | oil $n_D^{24}$: 1.6074 |
| 1.91 | H | H | —$CH_3$ | 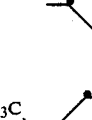 | m.p. 65–68° C. |
| 1.92 | 2-$CH_3$ | 5-Cl | —$CH_3$ |  | |
| 1.93 | H | H | —$CH_3$ | | |
| 1.94 | H | H | —$CH_2F$ | 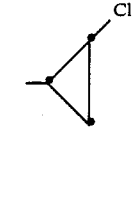 | m.p. 48–50° C. |

TABLE 1-continued
Compounds of the formula
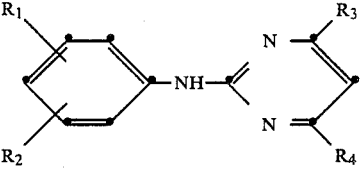
| Comp. no. | R₁ | R₂ | R₃ | R₄ | Physical constant |
|---|---|---|---|---|---|
| 1.95 | 2-OCH$_3$ | 5-Cl | —CH$_3$ |  | |
| 1.96 | 3-Cl | 4-OCH$_3$ | —CH$_3$ | 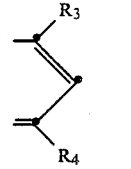 | |
| 1.97 | H | H | —CH$_2$CH$_2$OH | 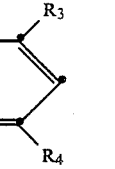 | |
| 1.98 | H | H | —CH$_3$ |  | |
| 1.99 | 2-Br | 4-Br | —CH$_3$ | 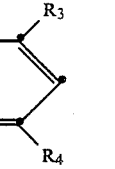 | |
| 1.100 | H | H | —CH$_2$F |  | m.p. 38–41° C. |
| 1.101 | 3-CH$_3$ | H | —CH$_3$ | 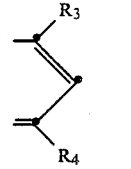 | |
| 1.102 | H | H | —C$_4$H$_9$-n |  | |
| 1.103 | 3-CH$_3$ | 4-Br | —CH$_3$ | 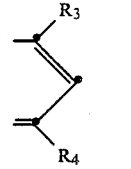 | |
| 1.104 | H | H | —C$_3$H$_7$-n |  | |

TABLE 1-continued
Compounds of the formula
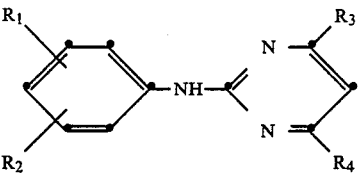
| Comp. no. | R₁ | R₂ | R₃ | R₄ | Physical constant |
|---|---|---|---|---|---|
| 1.105 | H | H | —CH₃ | | |
| 1.106 | H | H | —CH₂CH₂OH | | |
| 1.107 | 2-C₂H₅ | H | —CH₃ | | |
| 1.108 | H | H | —CH₂F | | m.p. 55–57° C. |
| 1.109 | H | H | H | | |
| 1.110 | H | H | —C₃H₇-n | | |
| 1.111 | 3-C₂H₅ | H | —CH₃ | | |
| 1.112 | H | H | —CH₂F | | |
| 1.113 | H | H | —CH₃ | | m.p. 83–85° C. |
| 1.114 | 2-Br | 5-Br | —CH₃ | | |

TABLE 1-continued
Compounds of the formula
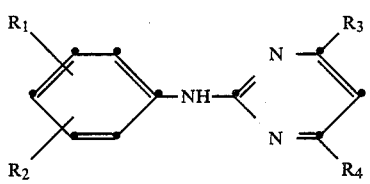
| Comp. no. | R$_1$ | R$_2$ | R$_3$ | R$_4$ | Physical constant |
|---|---|---|---|---|---|
| 1.115 | 2-CH$_3$ | 4-Br | —CH$_3$ | △ | |
| 1.116 | H | H | —C$_4$H$_9$-sek. | △-Cl | |
| 1.117 | 2-CH$_3$ | 5-F | —CH$_3$ | △ | |
| 1.118 | 4-C$_2$H$_5$ | H | —CH$_3$ | △ | |
| 1.119 | H | H | H | △-F | |
| 1.120 | H | H | —CH$_3$ | △(CH$_3$)$_2$ | m.p. 51–54° C. |
| 1.121 | 2-Br | 4-CH$_3$ | —CH$_3$ | △ | |
| 1.122 | H | H | —CH$_2$F | △(H$_3$C)(Cl)(Cl) | |
| 1.123 | H | H | —CF$_3$ | △-Br | |
| 1.124 | H | H | —CF$_3$ | △-Cl | |

TABLE 1-continued
Compounds of the formula
$$\underset{R_2}{\overset{R_1}{\bigcirc}}-NH-\overset{N=\underset{R_4}{\overset{R_3}{\diagup}}}{\underset{N=}{\diagdown}}$$
| Comp. no. | R₁ | R₂ | R₃ | R₄ | Physical constant |
|---|---|---|---|---|---|
| 1.125 | 2-C₃H₇-i | H | —CH₃ | 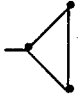 | |
| 1.126 | H | H | —CH₂F | 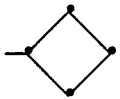 | m.p. 44–47° C. |
| 1.127 | H | H | —CH₃ | 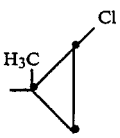 | |
| 1.128 | H | H |  | 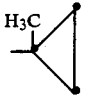 | m.p. 54–56° C. |
| 1.129 | 2-Cl | 4-Br | —CH₃ |  | |
| 1.130 | H | H | —C₄H₉-sek. |  | |
| 1.131 | H | H | —C₂H₅ |  | m.p. 57–59° C. |
| 1.132 | 4-C₃H₇-i | H | —CH₃ | 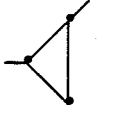 | |
| 1.133 | 2-OCH₃ | 5-CH₃ | —CH₃ | 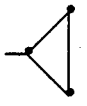 | |
| 1.134 | H | H | —CH₃ |  | |
| 1.135 | H | H | —CH₂Cl | 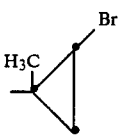 | |

TABLE 1-continued

Compounds of the formula

![structure with R1, R2 on phenyl-NH-C(=N)(N=)- pyrimidine with R3, R4]

| Comp. no. | R₁ | R₂ | R₃ | R₄ | Physical constant |
|---|---|---|---|---|---|
| 1.136 | 3-CF₃ | 5-CF₃ | —CH₃ | cyclopropyl | |
| 1.137 | H | H | —CF₃ | F-cyclopropyl | |
| 1.138 | H | H | —C₂H₅ | Br-cyclopropyl | |
| 1.139 | 2-CF₃ | H | —CH₃ | cyclopropyl | m.p. 56–58° C. |
| 1.140 | H | H | H | Cl-cyclopropyl | |
| 1.141 | H | H | —CH₃ | 2,2,3-trimethylcyclopropyl | |
| 1.142 | H | H | —CH₂Cl | Cl-cyclopropyl | |
| 1.143 | 2-Cl | 3-Cl | —CH₃ | cyclopropyl | |
| 1.144 | H | H | —C₄H₉-tert. | Cl-cyclopropyl | |
| 1.145 | H | H | —C₂H₅ | Cl-cyclopropyl | m.p. 55–60° C. |

TABLE 1-continued

Compounds of the formula

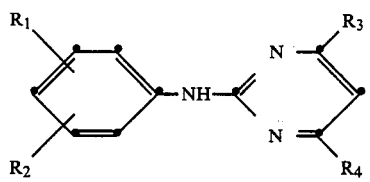

| Comp. no. | $R_1$ | $R_2$ | $R_3$ | $R_4$ | Physical constant |
|---|---|---|---|---|---|
| 1.146 | 2-CF$_3$ | 4-Cl | —CH$_3$ | cyclopropyl | |
| 1.147 | 2-Cl | 4-Cl | —CH$_3$ | cyclopropyl | |
| 1.148 | H | H | —CH$_3$ | 1-F,2-CH$_3$-cyclopropyl | |
| 1.149 | H | H | —CH$_2$Cl | 1-Br-cyclopropyl | |
| 1.150 | 3-CF$_3$ | H | —CH$_3$ | cyclopropyl | m.p. 81–83° C. |
| 1.151 | H | H | —C$_4$H$_9$-tert. | 1-CH$_3$-cyclopropyl | |
| 1.152 | 4-CF$_3$ | H | —CH$_3$ | cyclopropyl | m.p. 60–62° C. |
| 1.153 | 2-Cl | 5-CF$_3$ | —CH$_3$ | cyclopropyl | |
| 1.154 | H | H | —CH$_2$Cl | 2-F-cyclopropyl | m.p. 63–66° C. |
| 1.155 | H | H | —CH$_3$ | 1-CH$_3$,2,2-Cl$_2$-cyclopropyl | m.p. 99–109° C. |

TABLE 1-continued
Compounds of the formula
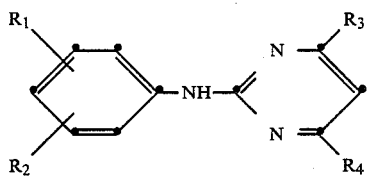
| Comp. no. | R₁ | R₂ | R₃ | R₄ | Physical constant |
|---|---|---|---|---|---|
| 1.156 | 2-Cl | 5-Cl | —CH₃ | △ | |
| 1.157 | 4-OC₃H₇-i | H | —CH₃ | △ | |
| 1.158 | H | H | —C₂H₅ | △F | m.p. 58–61° C. |
| 1.159 | 2-Cl | 6-Cl | —CH₃ | △ | |
| 1.160 | H | H | —C₂H₅ | △Cl | |
| 1.161 | H | H | —CH₃ | △(H₃C)(Br)(Br) | |
| 1.162 | H | H | —CH₂Cl | △Cl | m.p. 55–57° C. |
| 1.163 | 2-OCH₃ | H | —CH₃ | △ | |
| 1.164 | H | H | —CH₂CH₂CH₂Cl | △ | |
| 1.165 | H | H | H | △Br | |

TABLE 1-continued
Compounds of the formula
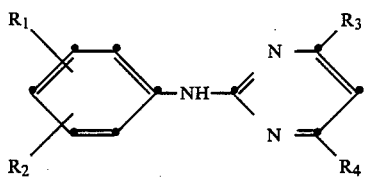
| Comp. no. | R₁ | R₂ | R₃ | R₄ | Physical constant |
|---|---|---|---|---|---|
| 1.166 | 2-F | 3-F | —CH₃ | cyclopropyl | |
| 1.167 | H | H | —C₂H₅ | 2-F-cyclopropyl | |
| 1.168 | H | H | —CH₃ | 1-Br-2,2-dimethyl-cyclopropyl (H₃C, CH₃, Br) | |
| 1.169 | H | H | —CH₂Cl | 1-Br-cyclopropyl | |
| 1.170 | 3-OCH₃ | H | —CH₃ | cyclopropyl | m.p. 47–50° C. |
| 1.171 | H | H | —CH₂Cl | 1,1-Cl₂-2-CH₃-cyclopropyl | |
| 1.172 | 2-CH₃ | 4-OCH₃ | —CH₃ | cyclopropyl | |
| 1.173 | 2-F | 4-F | —CH₃ | cyclopropyl | |
| 1.174 | H | H | —CH₂CH₂CH₂Cl | 1-CH₃-cyclopropyl | |
| 1.175 | H | H | —CH₃ | 1,2,2-trimethyl-cyclopropyl (H₃C, CH₃, CH₃) | |

TABLE 1-continued

Compounds of the formula

[Structure: R1,R2-substituted phenyl-NH-C(=N)(N=)-with R3, R4 substituents]

| Comp. no. | R₁ | R₂ | R₃ | R₄ | Physical constant |
|---|---|---|---|---|---|
| 1.176 | H | H | —CH₂Cl | CH₃, cyclopropyl with F | |
| 1.177 | 2-OCHF₂ | H | —CH₃ | cyclopropyl | |
| 1.178 | H | H | —CH₂OH | cyclopropyl with H₃C, Cl, Cl | |
| 1.179 | H | H | H | cyclopropyl with H₃C, Cl, Cl | |
| 1.180 | 2-F | 5-F | —CH₃ | cyclopropyl | oil |
| 1.181 | H | H | —CH₂OH | cyclopropyl with Cl, Cl | |
| 1.182 | H | H | —CH₃ | cyclopropyl with Br, CH₃, CH₃ | |
| 1.183 | H | H | —CHCl₂ | cyclopropyl with CH₃ | |
| 1.184 | 4-OCF₂CHF₂ | H | —CH₃ | cyclopropyl | |
| 1.185 | H | H | —CH₂Cl | cyclopropyl with Br, CH₃ | |

TABLE 1-continued
Compounds of the formula
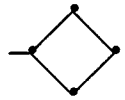
| Comp. no. | R₁ | R₂ | R₃ | R₄ | Physical constant |
|---|---|---|---|---|---|
| 1.186 | H | H | H | 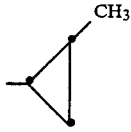 | |
| 1.187 | H | H |  CH₃ | 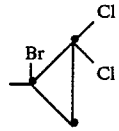 F | oil |
| 1.188 | H | H |  F | 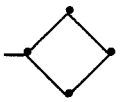 F | |
| 1.189 | H | H | —CH₃ |  Br, Cl, Cl | |
| 1.190 | 4-OCF₂CHClF | H | —CH₃ | 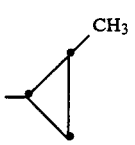 | |
| 1.191 | H | H | —CH₂Cl |  | |
| 1.192 | 2-F | 6-F | —CH₃ |  | |
| 1.193 | H | H | CH₃ | Cl | |
| 1.194 | 4-OC₃H₇-n | H | —CH₃ | | |
| 1.195 | H | H | F | Cl | |

TABLE 1-continued

Compounds of the formula

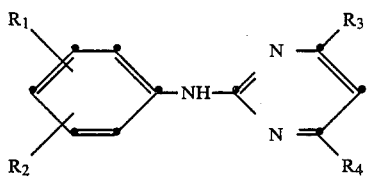

| Comp. no. | $R_1$ | $R_2$ | $R_3$ | $R_4$ | Physical constant |
|---|---|---|---|---|---|
| 1.196 | H | H | —CH$_3$ | cyclopropyl-Cl,Cl,Cl | |
| 1.197 | H | H | cyclopropyl-F | cyclopropyl-Cl | |
| 1.198 | 4-OCF$_2$CHCl$_2$ | H | —CH$_3$ | cyclopropyl | |
| 1.199 | H | H | cyclopropyl-F | cyclopropyl-CH$_3$ | |
| 1.200 | 3-F | 4-F | —CH$_3$ | cyclopropyl | oil |
| 1.201 | H | H | —CClF$_2$ | cyclopropyl | m.p. 68–70° C. |
| 1.202 | 3-OC$_2$H$_5$ | H | —CH$_3$ | cyclopropyl | |
| 1.203 | H | H | —CH$_3$ | cyclopropyl-Br,Br,Br | |
| 1.204 | H | H | —CH$_2$Br | cyclopropyl-F | |
| 1.205 | 4-OCF$_2$CFCl$_2$ | H | —CH$_3$ | cyclopropyl | |

TABLE 1-continued
Compounds of the formula
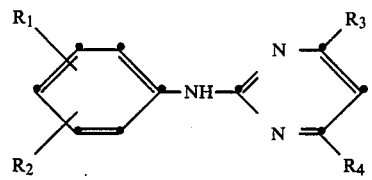
| Comp. no. | R₁ | R₂ | R₃ | R₄ | Physical constant |
|---|---|---|---|---|---|
| 1.206 | 2-OCH₃ | 5-OCH₃ | —CH₃ | cyclopropyl | |
| 1.207 | H | H | —CH₂OH | Br-cyclopropyl | |
| 1.208 | H | H | —CClF₂ | CH₃-cyclopropyl | |
| 1.209 | H | H | —CH₂Br | Cl-cyclopropyl | |
| 1.210 | 2-OCH₃ | 4-OCH₃ | —CH₃ | cyclopropyl | |
| 1.211 | H | H | CH₃-cyclopropyl | F-cyclopropyl | oil |
| 1.212 | H | H | —CH₂Br | Br-cyclopropyl | |
| 1.213 | H | H | F-cyclopropyl | F-cyclopropyl | |
| 1.214 | H | H | —CH₂OH | Cl-cyclopropyl | |
| 1.215 | H | H | CH₃-cyclopropyl | Cl-cyclopropyl | |

TABLE 1-continued

Compounds of the formula

| Comp. no. | R₁ | R₂ | R₃ | R₄ | Physical constant |
|---|---|---|---|---|---|
| 1.216 | 3-OCH₃ | 5-OCH₃ | —CH₃ | cyclopropyl | |
| 1.217 | H | H | —CH₂Br | F-cyclopropyl | |
| 1.218 | H | H | —CH₂CH(CH₃)CH₃ | cyclopropyl | m.p. 44–46° C. |
| 1.219 | 2-CH₃ | 3-CH₃ | —CH₃ | cyclopropyl | |
| 1.220 | H | H | —CH₂OH | F-cyclopropyl | |
| 1.221 | H | H | CH₃-cyclopropyl | Br-cyclopropyl | |
| 1.222 | H | H | —CH₂CH(CH₃)CH₃ | CH₃-cyclopropyl | |
| 1.223 | 2-CH₃ | 4-CH₃ | —CH₃ | cyclopropyl | |
| 1.224 | H | H | —CH₂Br | F-cyclopropyl | |
| 1.225 | H | H | cyclopropyl | Br-cyclopropyl | |

TABLE 1-continued

Compounds of the formula

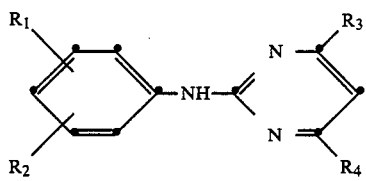

| Comp. no. | R$_1$ | R$_2$ | R$_3$ | R$_4$ | Physical constant |
|---|---|---|---|---|---|
| 1.226 | 2-CH$_3$ | 5-CH$_3$ | —CH$_3$ | cyclopropyl | |
| 1.227 | H | H | —CH$_2$OH | 1-Br-cyclopropyl | |
| 1.228 | H | H | —CF$_2$CF$_3$ | cyclopropyl | m.p. 50–52° C. |
| 1.229 | H | H | —CH$_2$OH | 1-Cl-cyclopropyl | |
| 1.230 | H | H | cyclopropyl | 1-Cl-cyclopropyl | |
| 1.231 | 2-CH$_3$ | 6-CH$_3$ | —CH$_3$ | cyclopropyl | |
| 1.232 | H | H | —CH$_2$Br | 1-Br-cyclopropyl | |
| 1.233 | H | H | —CF$_2$CF$_3$ | 1-CH$_3$-cyclopropyl | |
| 1.234 | H | H | 1-F-cyclopropyl | 1-CH$_3$-2,2-Cl$_2$-cyclopropyl | |
| 1.235 | H | H | 1-CH$_3$-cyclopropyl | 1-CH$_3$-cyclopropyl | m.p. 58–60° C. |

TABLE 1-continued
Compounds of the formula
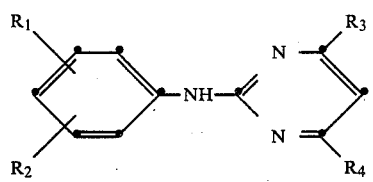
| Comp. no. | R1 | R2 | R3 | R4 | Physical constant |
|---|---|---|---|---|---|
| 1.236 | H | H | cyclopropyl | cyclopropyl | m.p. 75–77° C. |
| 1.237 | 3-CH3 | 4-CH3 | —CH3 | cyclopropyl | |
| 1.238 | H | H | —CH2OH | F-cyclopropyl | oil |
| 1.239 | H | H | —CH2Br | F-cyclopropyl-CH3 | |
| 1.240 | H | H | cyclopropyl | F-cyclopropyl | |
| 1.241 | H | H | cyclopropyl | F-cyclopropyl | |
| 1.242 | H | H | F-cyclopropyl | Cl-cyclopropyl | |
| 1.243 | H | H | —CH2Br | H3C-cyclopropyl-Cl,Cl | |
| 1.244 | H | H | Cl-cyclopropyl | H3C-cyclopropyl-Cl,Cl | |
| 1.245 | 3-CH3 | 5-CH3 | —CH3 | cyclopropyl | |

TABLE 1-continued

Compounds of the formula

![structure]

| Comp. no. | R1 | R2 | R3 | R4 | Physical constant |
|---|---|---|---|---|---|
| 1.246 | H | H | cyclopropyl | cyclopropyl with CH3 | oil $n_D^{25}$: 1,6232 |
| 1.247 | 3-F | 4-CH3 | —CH3 | cyclopropyl | |
| 1.248 | H | H | cyclopropyl | cyclopropyl with F | |
| 1.249 | H | H | —CH2Br | cyclobutyl | |
| 1.250 | 2-OCHF2 | 4-CH3 | —CH3 | cyclopropyl | m.p. 85–87° C. |
| 1.251 | 3-Cl | 4-OCHF | —CH3 | cyclopropyl | $n_D^{25}$ 1.5898 |
| 1.252 | 3-OCH3 | 4-OCH3 | —CH3 | cyclopropyl | m.p. 74–76° C. |
| 1.253 | H | H | —CH3 | cyclopropyl with F, Cl | m.p. 97–99° C. |

In Tables 2, 3 and 4 intermediate products, according to the invention, are exemplified.

TABLE 2

Compounds of the formula

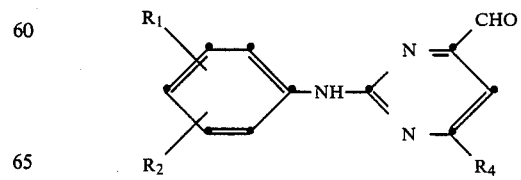

| Comp. no. | R1 | R2 | R4 | Physical constant |
|---|---|---|---|---|

| 2.1 | H | H |  | m.p. 112–114° C. |
|---|---|---|---|---|
| 2.2 | H | H | 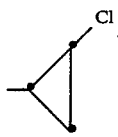 Cl | m.p. 123–127° C. |
| 2.3 | H | H | 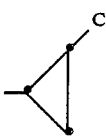 CH₃ | m.p. 87–90° C. |
| 2.4 | 4-Cl | H |  | |
| 2.5 | H | H | 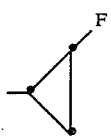 F | m.p. 128–132° C. |
| 2.6 | 3-F | H |  | |
| 2.7 | 4-F | H | 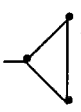 | |
TABLE 3
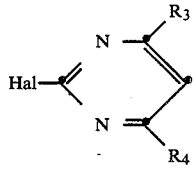
| Comp. no. | Hal | R₃ | R₄ | Physical constant |
|---|---|---|---|---|
| 3.1 | Cl | —CH₃ |  | m.p. 33–34° C. |
| 3.2 | Cl | —CH₃ |  CH₃ | oil; $n_D^{25}$: 1.5432 |
| 3.3 | Cl | —CH₃ | 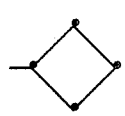 | |
TABLE 3-continued
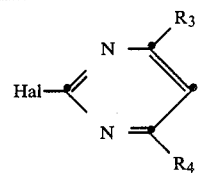
| Comp. no. | Hal | R₃ | R₄ | Physical constant |
|---|---|---|---|---|
| 3.4 | Cl | —CH₃ |  F | |
| 3.5 | Cl | —CH₃ | 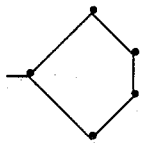 | |
| 3.6 | Cl | —C₃H₇-i | 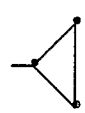 | |
| 3.7 | Cl | 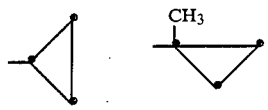 | CH₃ | |
| 3.8 | Cl | —CH₂—CH(CH₃)—CH₃ |  | |
| 3.9 | Cl | 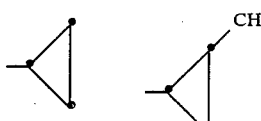 | CH₃ | |
| 3.10 | Br | —CH₃ | 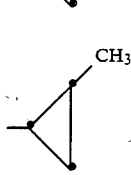 CH₃ | |
| 3.11 | Cl | H | 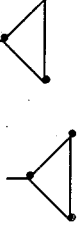 | |
| 3.12 | Cl | —C₄H₉-n | 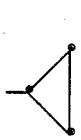 | |
| 3.13 | Cl | —CHCl₂ |  | |

TABLE 3-continued

[Structure: Hal-C(=N)-...-C(R3)=...-C(R4)=N ring]

| Comp. no. | Hal | R3 | R4 | Physical constant |
|---|---|---|---|---|
| 3.14 | Cl | —CH3 | 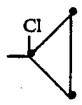 (cyclopropyl-Cl) | |
| 3.15 | Cl | —CH3 | 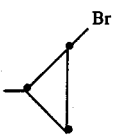 (cyclopropyl-Br) | |
| 3.16 | Cl | —CH3 | 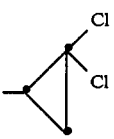 (cyclopropyl-Cl,Cl) | |
| 3.17 | Cl | —C2H5 | 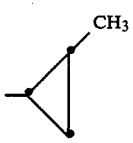 (cyclopropyl-CH3) | m.p. 32–35° C. |
| 3.18 | Cl | —CF2CF3 | 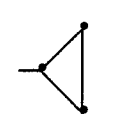 (cyclopropyl) | |
| 3.19 | Cl | —CH3 | 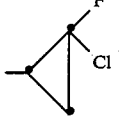 (cyclopropyl-F,Cl) | |
| 3.20 | Br | —CH3 | 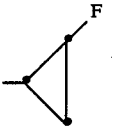 (cyclopropyl-F) | |
| 3.21 | Cl | —C2H5 | 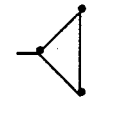 (cyclopropyl) | m.p. 28–31° C. |
| 3.22 | Cl | —CH3 | 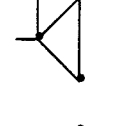 (cyclopropyl-CH3) | |
| 3.23 | Cl | —C4H9-sek. | 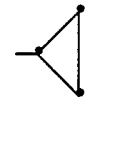 (cyclopropyl) | |

TABLE 3-continued

[Structure: Hal-C(=N)-...-C(R3)=...-C(R4)=N ring]

| Comp. no. | Hal | R3 | R4 | Physical constant |
|---|---|---|---|---|
| 3.24 | Cl | —CH3 | 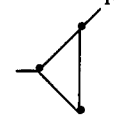 (cyclopropyl-F) | m.p. 42–45° C. |
| 3.25 | Cl | 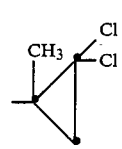 (cyclopropyl) | 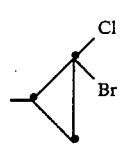 (cyclopropyl-CH3,Cl,Cl) | |
| 3.26 | Cl | —CH3 | 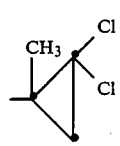 (cyclopropyl-Cl,Br) | |
| 3.27 | Cl | —CH3 | 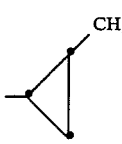 (cyclopropyl-CH3,Cl,Cl) | |
| 3.28 | Cl | 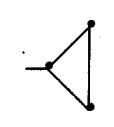 (cyclopropyl-CH3) | 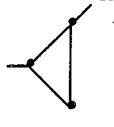 (cyclopropyl-CH3) | |
| 3.29 | Br | —CH3 | 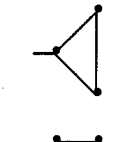 (cyclopropyl) | |
| 3.30 | Br | —CH3 | 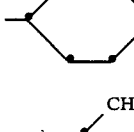 (cyclopropyl-Cl) | |
| 3.31 | Cl | —C3H7-n | 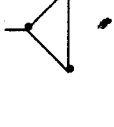 (cyclopropyl) | |
| 3.32 | Cl | —CH3 | (cyclohexenyl) | |
| 3.33 | Br | —C2H5 | (cyclopropyl-CH3) | |

TABLE 3-continued $$\text{Hal} - \underset{\underset{R_4}{\overset{N}{\|}}}{\overset{\overset{R_3}{\underset{\|}{N}}}{\bigcirc}}$$

| Comp. no. | Hal | $R_3$ | $R_4$ | Physical constant |
|---|---|---|---|---|
| 3.34 | Cl | $-CF_3$ | △ | |
| 3.35 | Br | $-C_2H_5$ | △ | |
| 3.36 | Cl | $-CH_3$ | △ with Cl | |
| 3.37 | Cl | $-CH_3$ | △ with F, F | |
| 3.38 | Cl | $-CH_3$ | △ with CH₃, CH₃ | |
| 3.39 | Cl | $-CClF_2$ | △ | |
| 3.40 | Cl | △ | △ | |
| 3.41 | Cl | $-CH_2Cl$ | △ | |
| 3.42 | Cl | $-CH_2F$ | △ | |
| 3.43 | Br | △ | △ | |
| 3.44 | Br | $-CH_2F$ | △ | |
| 3.45 | Cl | $-CH_2OH$ | △ | |
| 3.46 | Br | $-CH_2OH$ | △ | |

TABLE 4

$$R_5SO_2 - \underset{\underset{R_4}{\overset{N}{\|}}}{\overset{\overset{R_3}{\underset{\|}{N}}}{\bigcirc}}$$

| Comp. no. | $R_5$ | $R_3$ | $R_4$ | Physical constant |
|---|---|---|---|---|
| 4.1 | $CH_3$ | $-CH_3$ | △ | |
| 4.2 | $CH_3$ | $-CH_3$ | ◇ | |

TABLE 4-continued

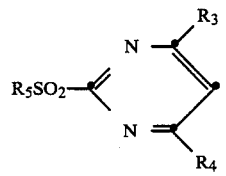

| Comp. no. | R$_5$ | R$_3$ | R$_4$ | Physical constant |
|---|---|---|---|---|
| 4.3 | C$_4$H$_9$-n | —CH$_3$ | cyclopropyl | |
| 4.4 | CH$_3$ | —CH$_3$ | Cl-cyclopropyl | |
| 4.5 | benzyl (CH$_2$–C$_6$H$_5$) | —CH$_3$ | cyclopropyl | |
| 4.6 | CH$_3$ | —CH$_3$ | Br-cyclopropyl | |
| 4.7 | –CH$_2$–C$_6$H$_4$–CH$_3$ | —CH$_3$ | cyclopropyl | |
| 4.8 | C$_2$H$_5$ | —CH$_3$ | F-cyclopropyl | |
| 4.9 | CH$_3$ | —CH$_3$ | Cl,Br-cyclopropyl | |
| 4.10 | CH$_3$ | CH$_3$-cyclopropyl | CH$_3$-cyclopropyl | m.p. 84–89° C. |
| 4.11 | CH$_2$–C$_6$H$_4$–Cl | —CH$_3$ | cyclopropyl | |
| 4.12 | CH$_3$ | —CH$_3$ | CH$_3$-cyclopropyl | |

TABLE 4-continued

R₅SO₂—C(=N—C(R₃)=C(R₄)—N=)

| Comp. no. | R₅ | R₃ | R₄ | Physical constant |
|---|---|---|---|---|
| 4.13 | CH₃ | —CH₃ | cyclopropyl with F | |
| 4.14 | CH₃ | —CH₃ | cyclopropyl with F, Cl | |
| 4.15 | C₂H₅ | —CH₃ | cyclopropyl with Cl | |
| 4.16 | CH₃ | —C₂H₅ | cyclopropyl | m.p. 64–68° C. |
| 4.17 | C₂H₅ | —CH₃ | cyclopropyl | |
| 4.18 | C₃H₇-n | —CH₃ | cyclopropyl | |
| 4.19 | CH₃ | —CH₃ | cyclopropyl with CH₃ | |
| 4.20 | C₃H₇-n | —CH₃ | cyclopropyl with CH₃ | |
| 4.21 | CH₃ | —CH₃ | cyclopropyl with F | |
| 4.22 | C₃H₇-n | —CH₃ | cyclopropyl with F | |

TABLE 4-continued $$R_5SO_2-\underset{N}{\overset{N}{\diagdown}}\underset{R_4}{\overset{R_3}{\diagup}}$$

| Comp. no. | $R_5$ | $R_3$ | $R_4$ | Physical constant |
|---|---|---|---|---|
| 4.23 | CH₃ | —CH₃ | cyclopropyl with 2F | |
| 4.24 | CH₃ | —C₂H₅ | cyclopropyl with CH₃ | |
| 4.25 | CH₃ | —CH₃ | cyclopropyl with Cl | |
| 4.26 | C₂H₅ | —CH₃ | cyclopropyl with CH₃ | |
| 4.27 | CH₃ | —CH₃ | cyclopropyl with 2Cl | |
| 4.28 | CH₃ | —CH₃ | cyclopropyl with 2CH₃ | |
| 4.29 | CH₃ | cyclopropyl | cyclopropyl | m.p. 54–58° C. |
| 4.30 | C₃H₇-n | —CH₃ | cyclopropyl with Cl | |

2. FORMULATION EXAMPLES FOR LIQUID ACTIVE INGREDIENTS OF FORMULA I (THROUGHOUT, PERCENTAGES ARE BY WEIGHT)

| 2.1. Emulsifiable concentrates | (a) | (b) | (c) |
|---|---|---|---|
| a compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2. Solutions | (a) | (b) | (c) | (d) |
|---|---|---|---|---|
| a compound of Table 1 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 2.3. Granulates | (a) | (b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by initimately mixing the carriers with the active ingredient.

Formulation Examples for solid active ingredients of formula I (throughout, percentages are by weight)

| 2.5. Wettable powders | (a) | (b) | (c) |
|---|---|---|---|
| a compound of Table 1 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of Table 1 | 10% |
| octylphenol polyethylene glycol ether (4-5 moles of ethylene oxide) | 3% |
| calcium dodecylbenzenesulfonate | 3% |
| castor oil polyglycol ether (35 moles of ethylene oxide) | 4% |
| cyclohexanone | 34% |
| xylene mixture | 50% |

Emulsions of any required concentration can be obtained from this concentrate by dilution with water.

| 2.7. Dusts | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carrier and grinding the mixture in a suitable mill.

| 2.8. Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound of Table 1 | 40% |
| ethylene glycol | 10% |
| nonyphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a aqueous emulsion | 75% 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

Example 3.1

Action against Venturia inaequalis on apple shoots
Residual protective action

Apple cuttings with 10–20 cm long fresh shoots are sprayed with a spray mixture (0.006% active ingredient) prepared from a wettable powder formulation of the test compound. The treated plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection.

Compounds of Table 1 exhibit good activity against Venturia (less than 20% attack). Thus e.g. compounds nos. 1.1, 1.6, 1.13, 1.14, 1.59, 1.66, 1.69, 1.84, 1.87, 1.94, 1.108, 1.126, 1.145, 1.158, 1.180, 1.200 and 1.236 reduce Venturia attack to 0 to 10%. On the other hand, Venturia attack is 100% in untreated and infected control plants.

Example 3.2

Action against Botrytis cinerea on apples Residual protective action

Artificially damaged apples are treated by the dropwise application to the damaged sites of a spray mixture (0.002% active ingredient) prepared from a wettable powder formulation of the test compound. The treated fruits are then inoculated with a spore suspension of the fungus and incubated for one week at high humidity and about 20° C. Evaluation is made by counting the rotted damaged sites and deriving the fungicidal activity of the test compound therefrom.

Compounds of Table 1 exhibit good activity against Botrytis (less than 20% attack). Thus e.g. compounds nos. 1.1, 1.6, 1.13, 1.14, 1.31, 1.33, 1.35, 1.48, 1.59, 1.66, 1.69, 1.84, 1.87, 1.94, 1.108, 1.126, 1.131, 1.145, 1.158, 1.180 and 1,236 reduce Botrytis attack to 0 to 10%. On the other hand, Botrytis attack is 100% on untreated and infected control plants.

Example 3.3

Action against Erysiphe graminis on barley Residual protective action

Barley plants about 8 cm in height are sprayed with a spray mixture (0.006% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

Compounds of Table 1 exhibit good activity against Erysiphe (less than 20% attack). Thus e.g. compounds nos. 1.1, 1.6, 1.13, 1.14, 1.35, 1.48, 1.59, 1.66, 1.69, 1.84, 1.87, 1.94, 1.108, 1.131, 1.158 and 1.236 reduce Erysiphe attack to 0 to 10%. On the other hand, Erysiphe attack is 100% on untreated and infected control plants.

Example 3.4

Action against Helminthosporium gramineum

Wheat grains are contaminated with a spore suspension of the fungus and dried. The contaminated grains are dressed with a suspension of the test compound prepared from a wettable powder (600 ppm of active ingredient, based on the weight of the seeds). Two days later the grains are placed in suitable agar dishes and the development of fungus colonies around the grains is assessed after another 4 days. The effectiveness of the test compounds is evaluated on the basis of the number and size of the colonies. The compounds of the Table substantially prevent fungus attack (0 to 10%).

Example 3.5

Action against Colletotrichum lagenarium on cucumbers

After a cultivation period of two weeks, cucumber plants are sprayed with a spray mixture (concentration 0.002%) prepared from a wettable powder formulation of the test compound. After two days the plants are infected with a spore suspension ($1.5 \times 10^5$ spores/ml) of the fungus and incubated for 36 hours at 23° C. and high humidity. Incubation is then continued at normal humidity and about 22°–23° C. Evaluation of fungus attack is made 8 days after infection. Fungus attack is 100% on untreated and infected control plants.

Compounds of Table 1 exhibit good activity and inhibit the spread of the disease. Fungus attack is reduced to 20% or less.

Example 3.6

(a) Contact action against Nephotettix cincticeps and Nilaparvata lugens (nymphs)

The test is carried out with growing rice plants. For this purpose 4 plants (14–20 days old) about 15 cm in height are planted into each of a number of pots (diameter 5.5 cm).

The plants are sprayed on a rotary table with 100 ml of an aqueous emulsion preparation containing 400 ppm of the test compound. After the spray coating has dried, each plant is populated with 20 nymphs of the test organisms in the third stage. To prevent the cicadas from escaping, a glass cylinder which is open at both ends is slipped over each of the plants and sealed with a gauze top. The nymphs are kept on the treated plants for 6 days until they have reached the adult stage. An evaluation is made on the basis of percentage mortality 6 days after population of the plants. The test is carried out at about 27° C. and 60% relative humidity. The plants are exposed to light for a period of 16 hours per day.

(b) Systemic action against Nilaparvata lugens (in water)

Rice plants about 10 days old (about 10 cm high) are placed in a plastics beaker which contains 150 ml of an aqueous emulsion preparation of the test compound in a concentration of 100 ppm and is closed by a perforated plastics lid. The roots of each of the rice plants are pushed through a hole in the plastics lid into the aqueous test preparation. Then the rice plants are populated with 20 nymphs of Nilaparvata lugens in the N2 to N3 stage and covered with a plastics cylinder. The test is carried out at about 26° C. and 60% relative humidity, and the plants are exposed to light for a period of 16 hours per day. After five days the number of dead test organisms is assessed in comparison with untreated controls. It is thus established whether the test substance absorbed via the roots kills the test organisms at the upper parts of the plants.

Compounds of Table 1 exhibit a pronounced killing action on the rice pests both in test a) and in test b). The mortality rate is 80% or above. Almost total mortality (98–100%) was achieved with compounds nos. 1.1, 1.6, 1.14, 1.59, 1.66, 1.87, 1.94, 1.108 and 1.236.

What is claimed is:

1. A compound of the formula

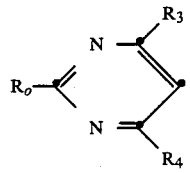

in which:
$R_o$ is halogen or $R_5$—$SO_2$—; $R_3$ is hydrogen; $C_1$–$C_4$alkyl; or $C_1$–$C_4$alkyl substituted by halogen, hydroxy or by cyano; cyclopropyl; or cyclopropyl mono- to tri-substituted by methyl and/or by halogen; $R_4$ is
$C_3$–$C_6$cycloalkyl or
$C_3$–$C_6$cycloalkyl mono- to tri-substituted by methyl and/or by halogen; and
$R_5$ is $C_1$–$C_8$alkyl or benzyl that is unsubstituted or substituted by halogen and/or by $C_1$–$C_4$alkyl.

* * * * *